US009488639B2

(12) United States Patent
Lange et al.

(10) Patent No.: US 9,488,639 B2
(45) Date of Patent: Nov. 8, 2016

(54) CELL-BASED TISSUE ANALYSIS

(71) Applicant: Flagship Biosciences, Inc., Westminster, CO (US)

(72) Inventors: Holger Lange, Enger (DE); Joseph Krueger, Andover, MA (US); George David Young, Boulder, CO (US); Trevor Johnson, San Diego, CA (US); Frank Voelker, Brewster, MA (US); Steven Potts, Phoenix, AZ (US)

(73) Assignee: FLAGSHIP BIOSCIENCES, INC., Westminster, CO (US)

( * ) Notice: Subject to any disclaimer, the term of this patent is extended or adjusted under 35 U.S.C. 154(b) by 52 days.

(21) Appl. No.: 13/934,237

(22) Filed: Jul. 3, 2013

(65) Prior Publication Data

US 2015/0004630 A1    Jan. 1, 2015

Related U.S. Application Data

(60) Provisional application No. 61/769,049, filed on Feb. 25, 2013.

(51) Int. Cl.
| | |
|---|---|
| *G01N 33/50* | (2006.01) |
| *G01N 15/14* | (2006.01) |
| *G06K 9/00* | (2006.01) |
| *G01N 35/00* | (2006.01) |
| *G01N 15/10* | (2006.01) |

(52) U.S. Cl.
CPC ...... *G01N 33/5005* (2013.01); *G01N 15/1463* (2013.01); *G06K 9/0014* (2013.01); *G06K 9/00147* (2013.01); *G01N 2015/1006* (2013.01); *G01N 2035/00138* (2013.01)

(58) Field of Classification Search
CPC ................ G01N 33/5005; G01N 15/1463; G01N 2035/00138; G01N 2015/1006; G06K 9/0014; G06K 9/00147
See application file for complete search history.

(56) References Cited

U.S. PATENT DOCUMENTS

| | | | |
|---|---|---|---|
| 7,899,624 B2 * | 3/2011 | Cualing et al. | ................. 702/19 |
| 8,787,651 B2 * | 7/2014 | Potts et al. | .................... 382/133 |
| 2005/0111758 A1 | 5/2005 | Lange | |
| 2008/0240558 A1 | 10/2008 | Li | |
| 2012/0076390 A1 | 3/2012 | Potts | |

FOREIGN PATENT DOCUMENTS

| | | |
|---|---|---|
| RU | 2332223 | 8/2008 |
| WO | WO03059272 | 7/2003 |

* cited by examiner

*Primary Examiner* — Gail R Gabel
(74) *Attorney, Agent, or Firm* — Coastal Patent Law Group, P.C.

(57) ABSTRACT

Methods for cell-based tissue analysis utilize modern trends in digital microscopy to obtain, process, calibrate, and analyze digital images of tissue sections to quantify cell-based data for improved histological analysis. Using data from multiple images of a common tissue section, or data from images of multiple tissue sections, additional degrees of freedom are realized and the resulting analysis provides added depth to histological analysis of tissue samples. With computerized analytical methods, speed and accuracy of histological analysis is greatly improved.

11 Claims, 23 Drawing Sheets

Virtual Cells and Cells from different Tissue Sections

Cells

Tissue Section 1 Cells    Tissue Section 2 Cells    Tissue Section 3 Cells

Tissue Section 1    Tissue Section 2 Common Grid    Tissue Section 3

Common Grid

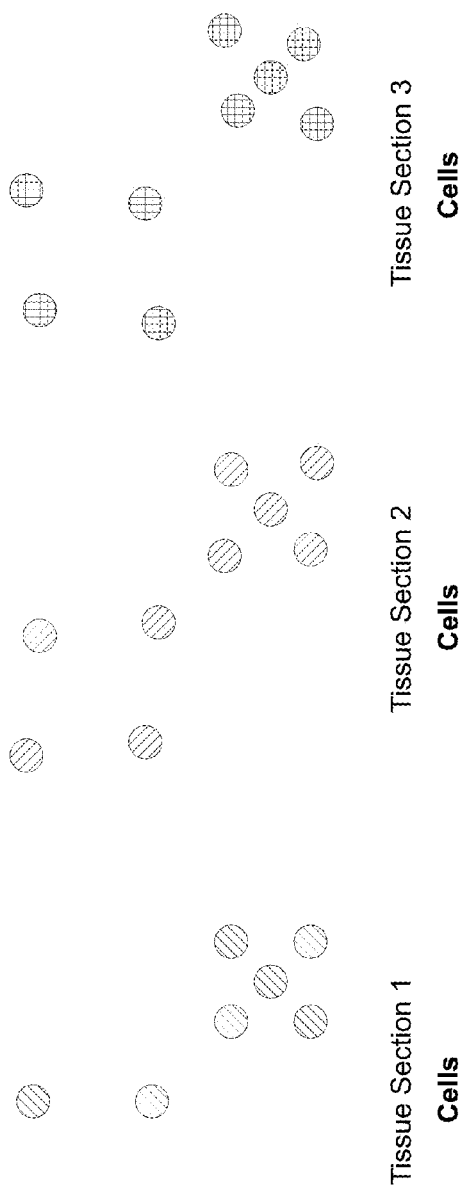
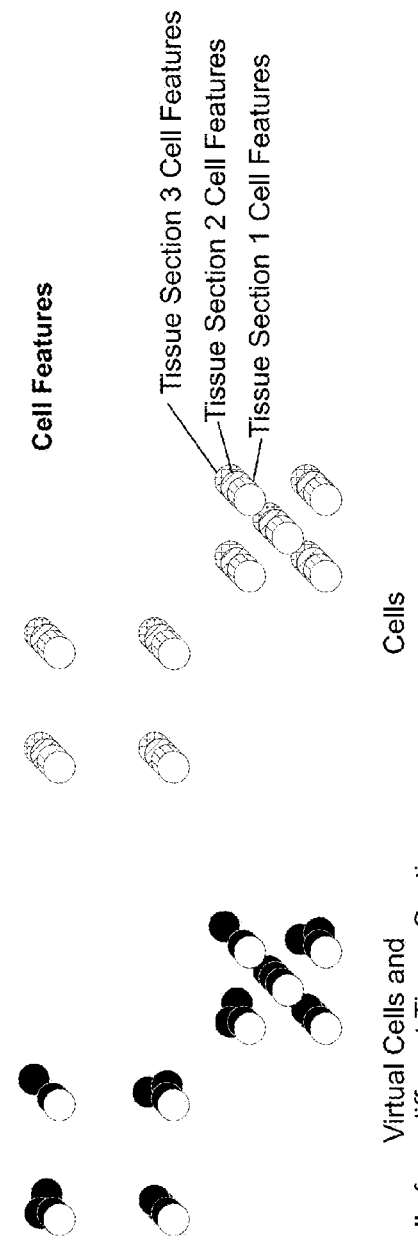
Fig. 13A
Fig. 13B

|  | Select Items | Options | Sort | | | | | | | | |
|---|---|---|---|---|---|---|---|---|---|---|---|
| Meta Data | | | | ■ | ■ | ■ | ■ | ■ | ■ | ■ | ■ |
| Species | | | | 1 | 2 | 3 | 4 | 5 | 6 | 7 | 8 |
| Tissue Type | | | | A | A | B | B | A | B | A | B |
| Clinical Outcome | ▶ | xxx ▶ | ▶ | | | | | | | | |
| Treatment Option | | yyy ▶ | ▶ | | | | | | | | |
| Cell Population Data | | | | ■ | ■ | ■ | ■ | ■ | ■ | ■ | ■ |
| Cell Population A | ▶ | ▶ | ▶ | | | | | | | | |
| Feature X | ▶ | ▶ | ▶ | | | | | | | | |
| Feature Y | | ▶ | ▶ | | | | | | | | |
| Feature Z | | | ▶ | | | | | | | | |
| Cell Population B | ▶ | ▶ | ▶ | ■ | ■ | ■ | ■ | ■ | ■ | ■ | ■ |
| Feature U | | | | | | | | | | | |
| Cell Data | | | | ■ | ■ | ■ | ■ | ■ | ■ | ■ | ■ |
| Slide Images | | | | ■ ■ | ■ ■ | ■ ■ | ■ ■ | ■ ■ | ■ ■ | ■ ■ | ■ ■ |

CELL-BASED TISSUE ANALYSIS

CROSS-REFERENCE TO RELATED APPLICATIONS

This application claims benefit of priority with U.S. Provisional Application Ser. No. 61/769,049, filed Feb. 25, 2013, and titled "CELL-BASED TISSUE ANALYSIS"; the contents of which are hereby incorporated by reference.

BACKGROUND OF THE INVENTION

1. Field of the Invention

This invention relates generally to medical imaging; and more particularly, to methods for computerized analysis of microscopic images of tissue sections.

2. Description of the Related Art

As before in radiology, now with the digitization of pathology, with more precise imaging of histology slides, new computer-assisted methods can be used that go far beyond the ability of human evaluation and interpretation of a glass slide using optical microscopy.

Sophisticated image analysis programs can be used to detect and characterize cells on partial or entire tissue sections and define and characterize different cell populations of a tissue specimen. Tissue specimens can then be examined and evaluated based on those cell populations in the context of other tissue specimens (study data set, target patient population data sets, etc.). Ultimately, a pathologist or tissue analyst can use the data from this approach in making assessments on endpoint determinants of the evaluation.

Similar concepts are used in flow cytometry, where multi-dimensional information is captured on every cell identified, and the dimensions are gated and compared to each other to define specific attributes of cell features. In contrast to flow cytometry, which relies on the physical capture and special instrumentation for the analysis of dissociated cells, image-based cell sorting does not rely on the physical capture and analysis of each cell as it is done digitally. Also, analysis of cells in their tissue section context has the advantage of maintaining the information of structural morphology of the tissue and context of the cells, while not requiring a special instrument.

There is a present and continuing need for systems and methods to build an image-based tissue analysis tool, which can be used to study multiple cell dimensions within a tissue to identify relationships between cells within and between tissue sections.

SUMMARY OF THE INVENTION

In accordance with the embodiments herein, novel methods for examining tissue specimens based on histology slides are provided that go far beyond the ability of human evaluation and interpretation using an optical microscope, the methods generally comprise: detecting and characterizing cells on partial or entire tissue sections, defining and characterizing different cell populations of a tissue specimen, and examining tissue specimens based on cell population characteristics.

These as well as other features and advantages are described in the following detailed description of the preferred embodiments.

BRIEF DESCRIPTION OF THE DRAWINGS

Certain embodiments are described with reference to the following figures, wherein:

FIG. 13(A-B) illustrates the mapping of cell features across different tissue sections using virtual cells.

FIG. 21 illustrates a heatmap for tissue samples from a database.

DETAILED DESCRIPTION OF PREFERRED EMBODIMENTS

In the following description, for purposes of explanation and not limitation, details and descriptions are set forth in order to provide a thorough understanding of the present invention. However, it will be apparent to those skilled in the art that the present invention may be practiced in other embodiments that depart from these details and descriptions without departing from the spirit and scope of the invention.

Certain methods and systems are described for examining tissue specimens based on histology slides using simultaneous multi-parametric analysis of the characteristics of the cells and cell populations from partial or entire tissue sections.

Figure 1:
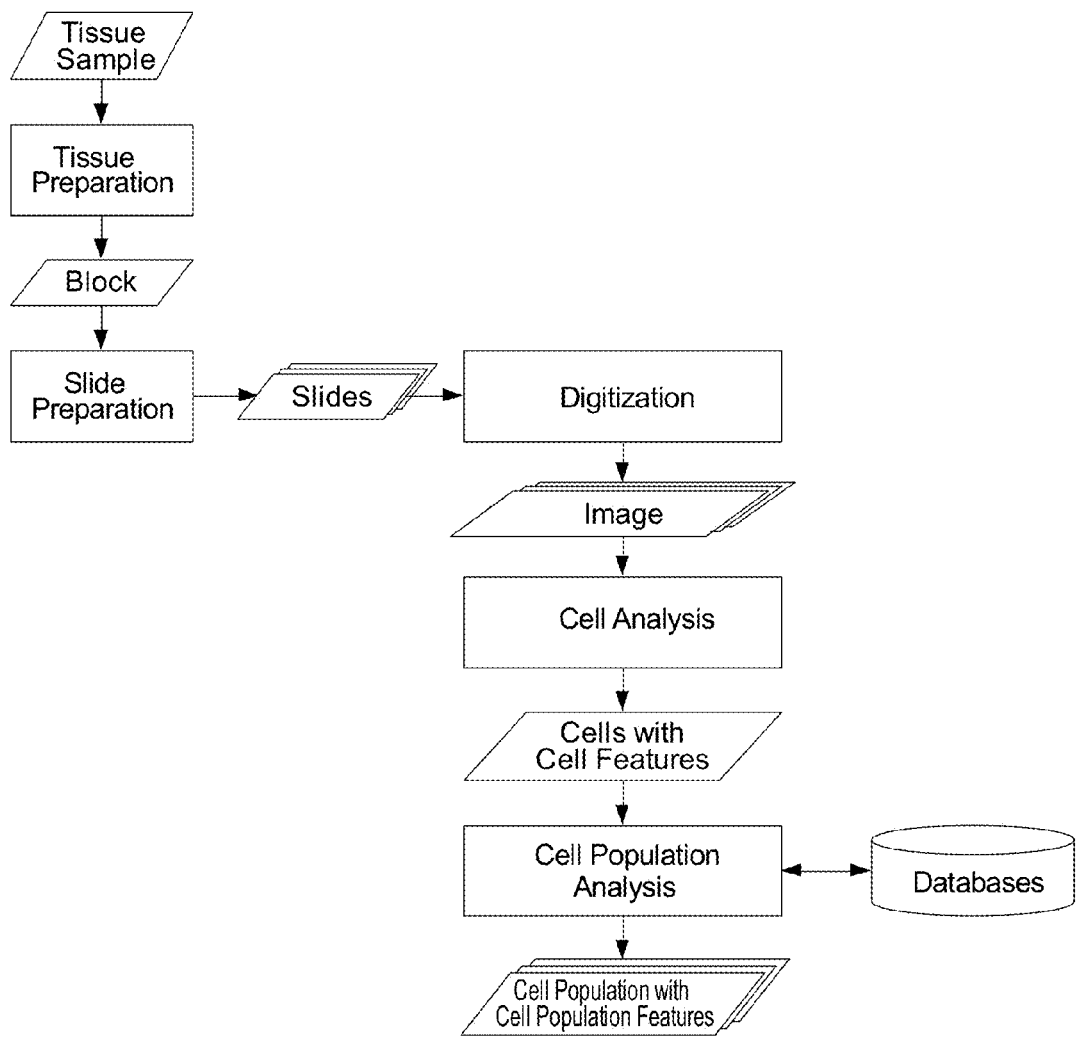
FIG. 1 shows a flowchart of the entire cell-based tissue analysis process from a tissue sample to the cell population analysis.

In an illustrative embodiment, the method may generally comprise five consecutive processing steps, including: (1) tissue preparation; (2) slide preparation; (3) digitization; (4) cell analysis; and (5) cell population analysis. FIG. 1 shows a flowchart of the entire cell-based tissue analysis process from a tissue sample to the cell population analysis in accordance with a general embodiment.

Tissue Preparation

The tissue preparation process comprises: collection/acquisition of a tissue specimen or sample (e.g. biopsy, excision, surgical specimen), fixation of the tissue sample (e.g. using a fixative such as formalin), transporting the sample to a histology laboratory, creating a tissue block in which the tissue is embedded in a specified media. For purposes herein, a "tissue specimen" or "sample under investigation" may be referred to as a "tissue sample". A similar process is followed in the collection and preparation of frozen tissue samples, with the exception of freezing media is utilized instead of fixation media resulting in a frozen tissue sample which is processed to a tissue slide using standard and accepted histological procedures.

This tissue preparation process can have a considerable effect on how the cell features of interest will be expressed in the tissue sections. Careful control needs to be applied to standardize this process.

Slide Preparation

The slide preparation process comprises standard and accepted histological procedures: the cutting of the tissue block into tissue sections that are placed on glass slides (aka histology slides) and subsequently the staining of the slides (e.g. Hematoxylin and Eosin—H&E, Immunohistochemistry—IHC, etc.) to make the specific cell features of interest detectable by the cell analysis.

Multiple tissue sections can be cut from a single tissue block whereby each tissue section is typically stained for a specific purpose (e.g. H&E for tissue and cell morphology, IHC-HER2 for the quantification of the protein expression of the Human Epidermal growth Receptor 2, IHC-ER for the quantification of the protein expression of the estrogen receptor, IHC-PR for the quantification of the protein expression of progesterone receptor).

The cutting of the tissue block (e.g. depth) and the staining process itself can have a considerable effect on how the cell features of interest are expressed in the tissue sections. Careful control needs to be applied to standardize this process.

Standardized tissue-based or equivalent (e.g. cell lines) controls with different established expression levels (e.g. 0%, 25%, 50% and 75%) of a cell feature (e.g. cell expressions, cell neighborhood characteristics, cell morphology) can be used as part of each staining batch (either on a separate slide or on all slides) to allow the cell analysis programs to automatic calibrated the cell feature measurements. The key is that the controls exhibit similar cell features as contained in the tissue samples.

One possible choice for a tissue-based control is to use samples from the target tissue. The key is to use samples with different cell feature expression levels and to establish the proper target values for those samples. Establishing the target values for new controls can be done using existing controls. Using this method, special care needs to be taken not to introduce a bias that accumulates from one control to the next.

In the past, the staining of histology slides had been designed for human interpretation using optical microscopes. Additional information may be obtained using specialized analytical tools, such as electron microscopy and confocal microscopy, but these are generally not utilized in a high throughput or general laboratory/histology environment. Using sophisticated image analysis programs to analyze the images of histology slides imposes different requirements on the staining. Special care needs to be taken in the choice of stains and their staining procedures. The choice of stains will be driven by how well color separation programs (e.g. color deconvolution) can distinguish them from each other and how well they can be resolved when the stains are colocalized. Determining the right staining procedure will be driven by providing a consistent and detectable staining across the target area (e.g. nucleus). Since different procedures can result in different color hues and intensities for the same descriptive staining process (such as Hematoxylin counterstaining), a standardized staining procedure needs to be followed to avoid variability in interpretation of the staining In some cases it may be appropriate to provide two histology slides, one stained for human interpretation using standard optical microscopes and one stained for the use of image analysis programs. In either case, the purpose of the standardization is to ensure for reliable subject interpretation by a human or consistent objective interpretation by an image analysis program.

Digitization

Histology slides can be digitized using commercially available digital microscopes and/or slide scanners (e.g. Aperio, Cri, Hamamatsu, Leica, Omnyx, Philips, Ventana and 3DHistech). Different imaging acquisition techniques (e.g. brightfield, fluorescence, multi-spectral, polarized) can be used to create a digital image of a histology slide. In some cases, different image acquisition techniques can be applied to the same histology slide resulting into multiple images for a single slide. The digitization of a slide can have a considerable effect on how the cell features of interest are imaged. Careful control needs to be applied to standardize this process.

Assuming that the specific image acquisition characteristics of the instruments are well controlled by each of the manufacturers, still instruments from different manufacturers exhibit sometimes considerable variations in their image acquisition characteristics.

Color is one of the most important image acquisition characteristics for the cell analysis of stained tissue sections. Standardized color calibration slides with established color target values that are representative for the color spectrum of the used stains or dyes can be used as part of a periodically repeated (e.g daily) instrument calibration procedure. The difference of the measured color values and the established target values can be used to define a color calibration profile (e.g. ICC profile) that can be applied to the images prior to the cell analysis to normalize all images to a standard color space (e.g. sRGB) for the image analysis.

One possible choice for a color calibration target is to use existing standard color calibration targets (e.g. IT8). The problem is that those are not representative for the color spectrum of the used stains or dyes. A better way is to measure the color characteristics of the stains or dyes and to create specific color calibration targets.

Figure 2:
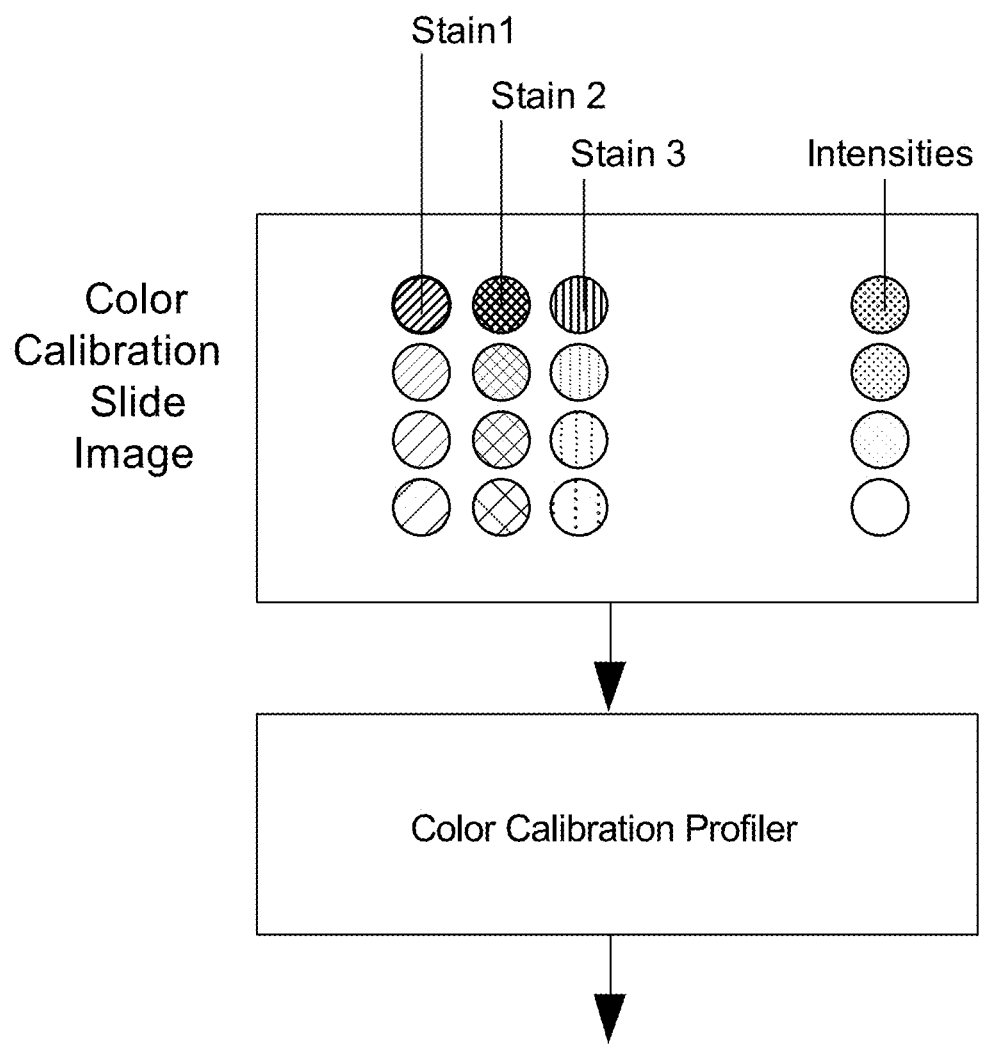
FIG. 2 illustrates the color calibration profile generation from a stain specific color calibration target.

FIG. 2 illustrates the color calibration profile generation from a stain specific color calibration target. A brightfield RGB image acquisition and the use of the sRGB color space as the standard color space for image analysis is assumed. The color calibration target shown includes three stains with single stain color patches of different staining intensities and gray scale patches of different intensities for all of which the target colors have been established in sRGB color space. A color calibration profiler program analyses the different patches in the image of the color calibration target and determines, based on the differences between the measured RGB color values and the established target sRGB color values a color calibration profile in form of a look-up table.

One possible application would be to include Hematoxylin, Eosin and DAB as the stains for the stain-specific color calibration target.

Important image acquisition characteristics that cannot be calibrated, including the spatial resolution, need to be measured and monitored using special calibration slides as part of a periodically repeated (e.g daily) instrument calibration verification procedure. It is important to make sure that the instrument is operating properly and that the required assumptions for the subsequent cell analysis hold true.

Cell Analysis

The cell analysis program includes the detection of the cells and the calculation of the cell features in the images from the different tissue sections. The cell analysis is typically application-specific to species (e.g. human), the tissue type (e.g. round cells in breast tissue vs. elongated cells in gastrointestinal tissue), the cell compartments being stained (nucleus, membrane and cytoplasm), the staining (e.g. Hematoxylin, Eosin, DAB) and the image acquisition (e.g. brightfield, fluorescence, multi-spectral, polarized).

A key idea of the cell-based tissue analysis is that it can include the structural and contextual tissue morphology of the cells in the analysis. The cell features typically include the cell morphology, features that represent a cell's physical presentation on the slide (e.g. cell size), expressions of biomarkers (e.g. protein, gene and mRNA), and the staining (e.g. Hematoxylin counterstaining). However, cell features are also measured from the cells in a defined neighborhood around the cell, which includes the measurements of the combined groupings of cells to define tissue characteristics (e.g. cell density).

Figure 3:
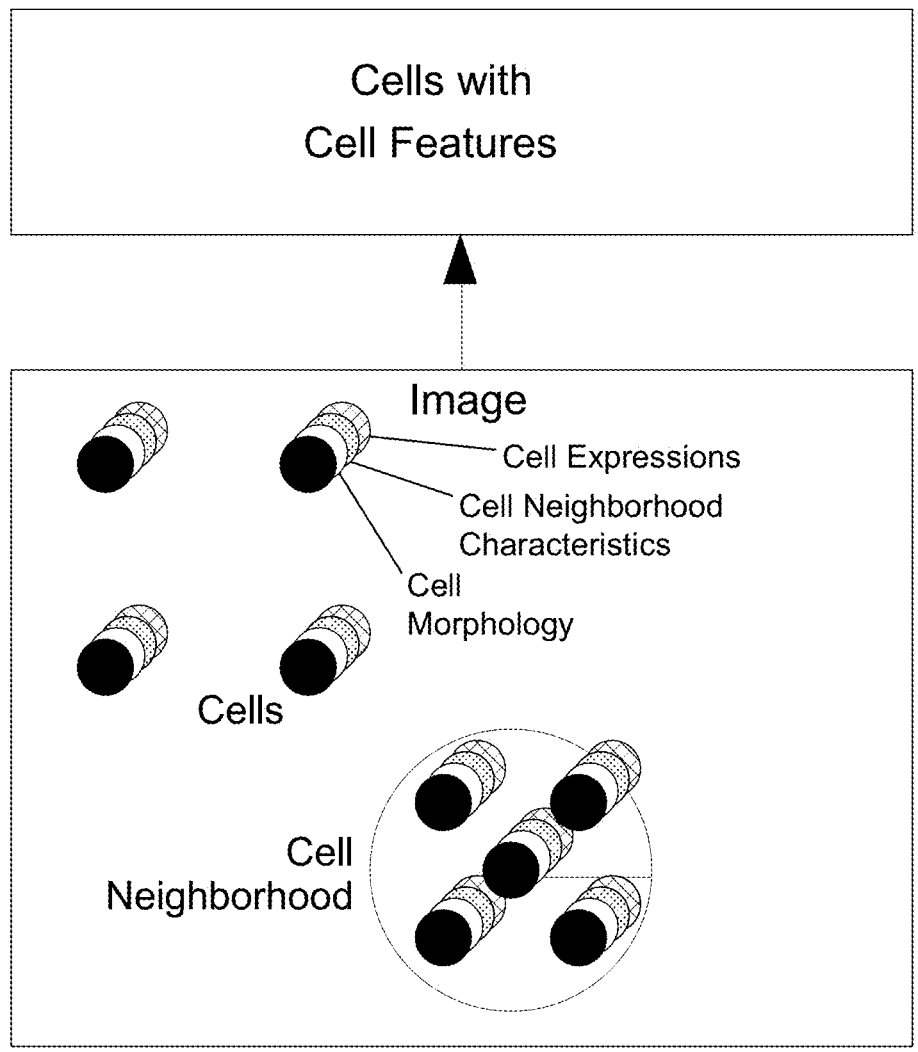
FIG. 3 shows the data hierarchy associated with the cell analysis.

FIG. 3 shows the data hierarchy associated with the cell analysis. The cells (black circles) are detected in an image from a tissue section. The cell features (e.g. cell morphology, cell neighborhood characteristics, cell expressions) are calculated based on measurements of the cell itself as well as the cells in a neighborhood around the cell and are depicted as distinct greyscale patterns. The neighborhood of a cell is illustrated by the circle with a radius around a cell.

Visualization

The cells with their cell features can be visualized in many different ways, including intensity/color-coded cell representations (e.g. bitmap of detected cells and cell compartments, circles, ellipses) and heatmaps overlaid on the images from the different tissue sections, 1D, 2D and 3D data plots and sortable and searchable data tables.

Figure 4:
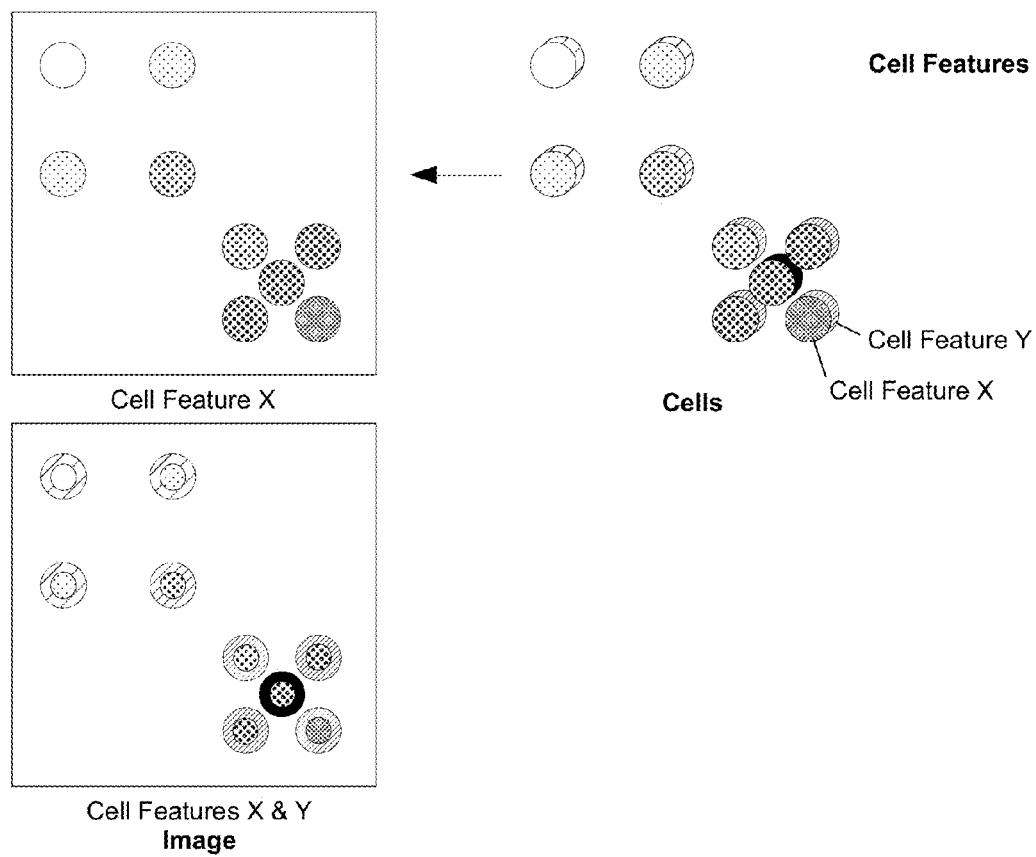
FIG. 4 illustrates the display of cell representations with intensity-coded cell features overlaid on an image.

FIG. 4 illustrates the display of cell representations with intensity-coded cell features overlaid on an image. Cells with two cell features "X" and "Y" are shown. The top image shows a cell representation in form of a circle, which is intensity-coded based on cell feature "X". Multiple cell features can be visualized at the same time. The bottom image shows a cell representation in form of two nested circles. The inner circle is intensity-coded based on cell feature "X". The outer circle is intensity-coded based on cell feature "Y".

Figure 5:
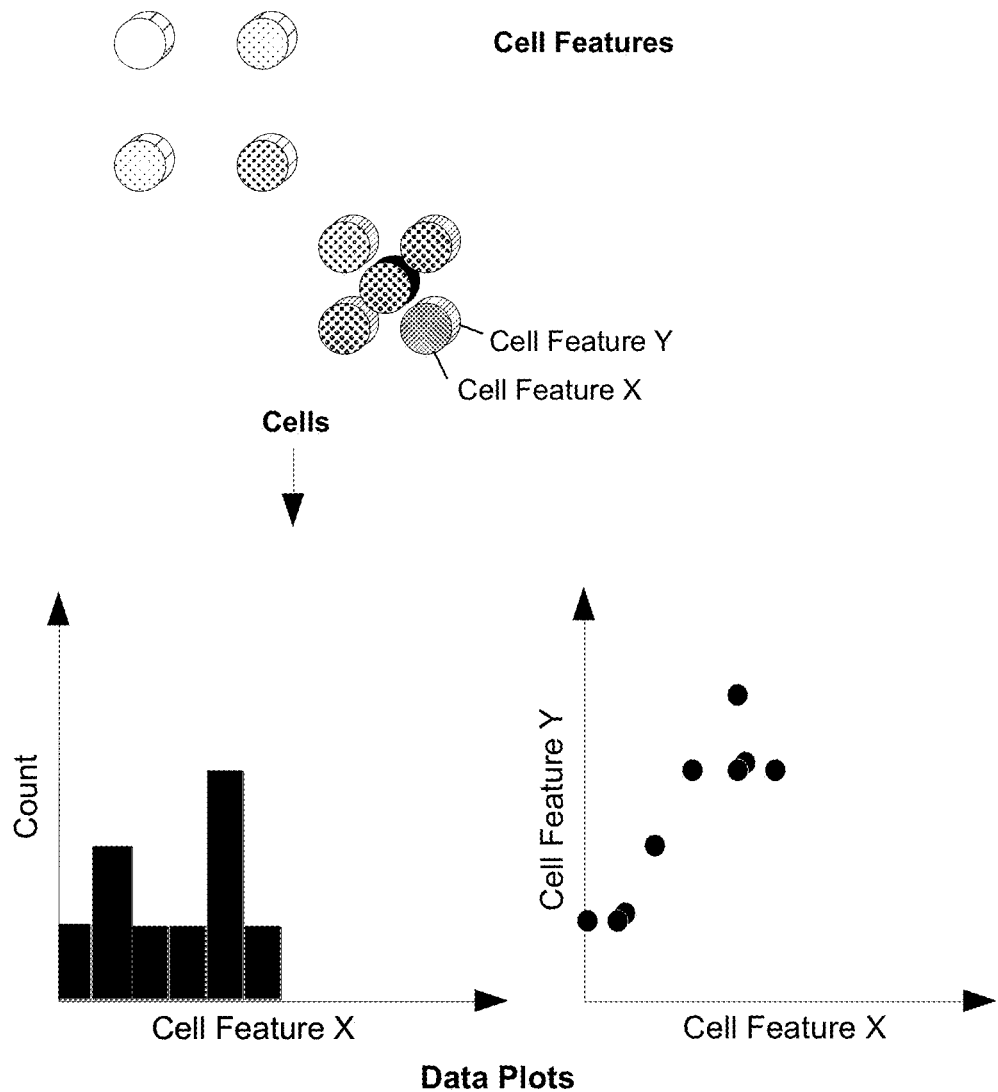
FIG. 5 illustrates the display of cell feature data plots.

FIG. 5 illustrates the display of cell feature data plots. The left data plot shows a 1D histogram of the values from cell feature "X". The right data plot shows a 2D scatter plot of the values from cell features "X" and "Y".

Figure 6:
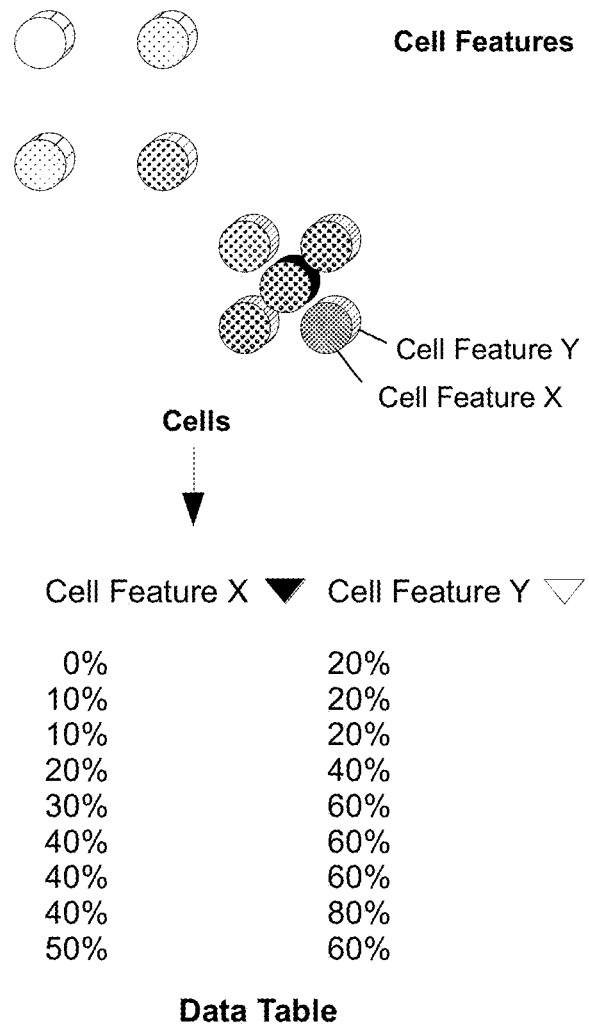
FIG. 6 illustrates the display of cell feature data tables.

FIG. 6 illustrates the display of cell feature data tables. The cells and the cell features are displayed as a list in a table with a row for each cell and the cell features "X" and "Y" as the columns. The cells are sorted by the cell feature "X".

A cell-based heatmap provides high-resolution data in regions of high cell density. The cell feature values are propagated in a certain distance around the cells. The propagation is stopped at the maximum distance or equal distance to another cell.

Figure 7:
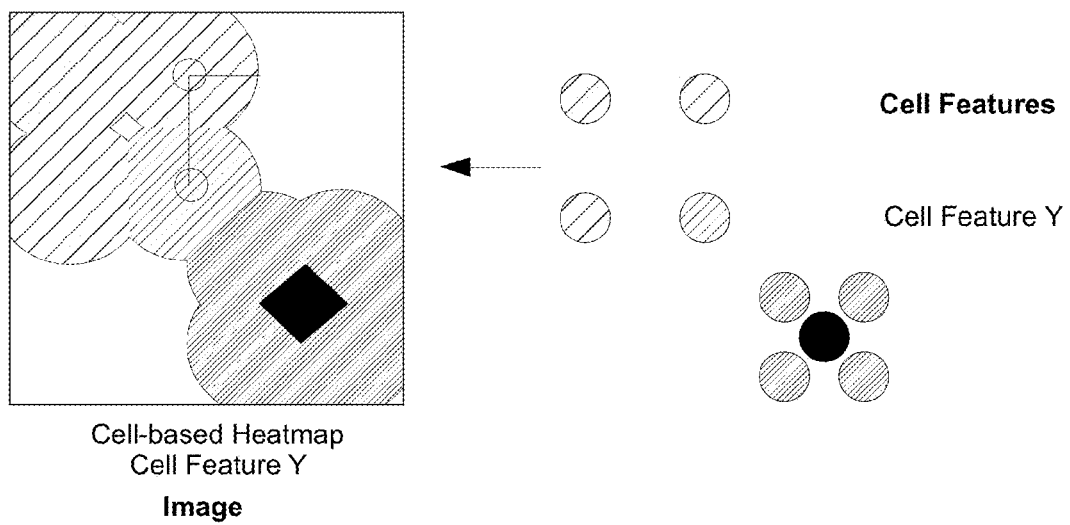
FIG. 7 illustrates the display of cell-based heatmaps overlaid on an image.

FIG. 7 illustrates the display of cell-based heatmaps overlaid on an image.

The cell analysis can provide an interactive linkage of the cells between the cells overlaid in the images, the cells in the data plots and the cells in the data tables. Cells can be selected in one of those data representations and those cells will be identified automatically in the other data representations.

Figure 8A:
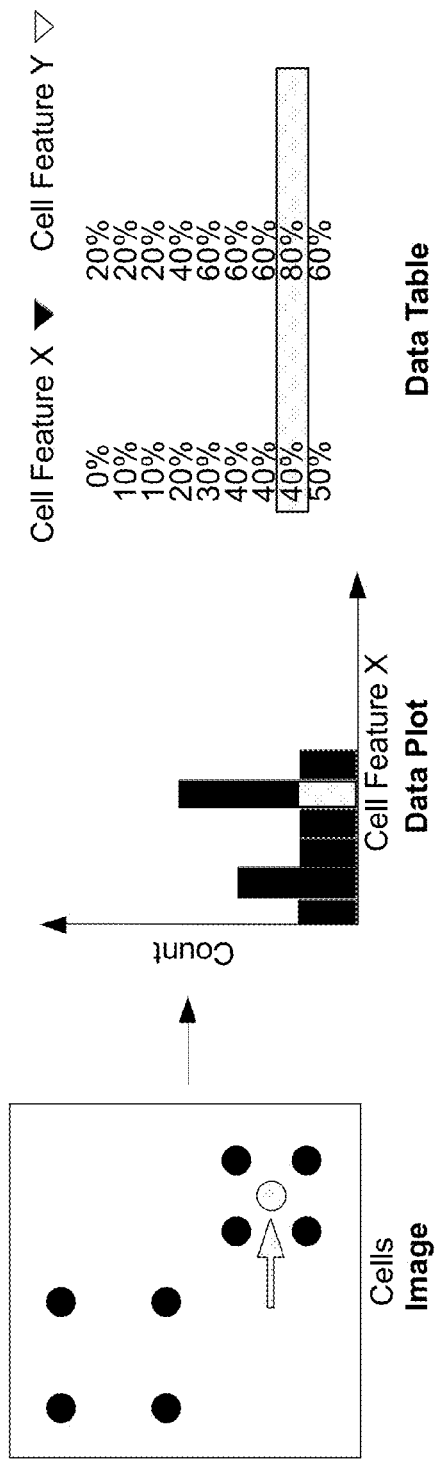
FIG. 8(A-B) illustrates the interactive linkage of the cells between different data representations.
Figure 8B:
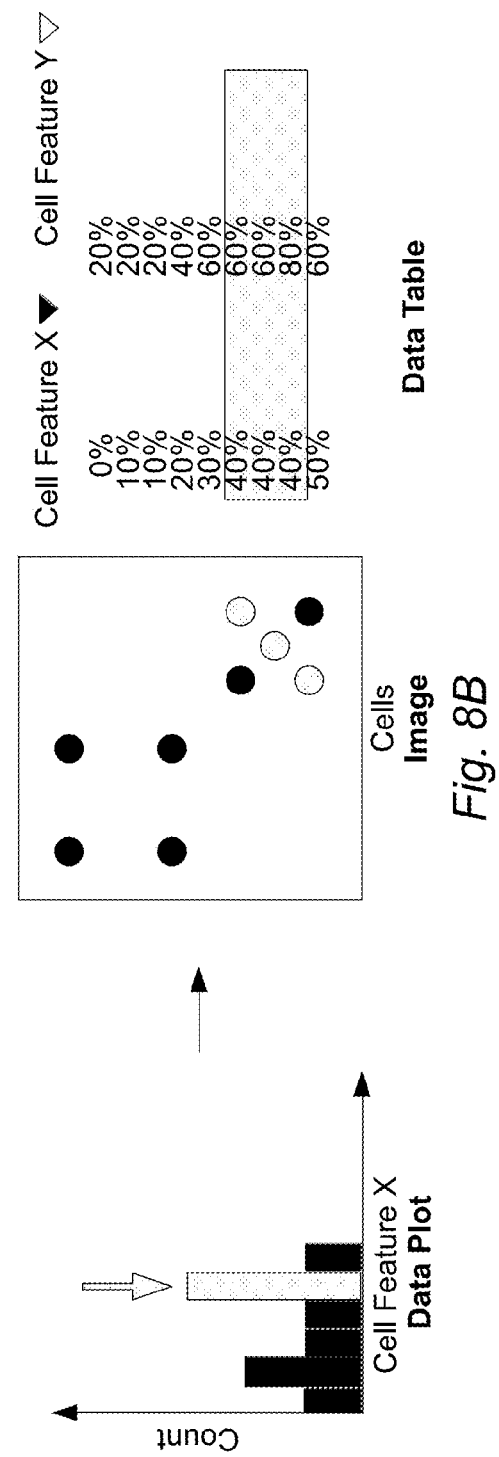

FIG. 8 illustrates the interactive linkage of the cells between different data representations. FIG. 8A shows that when a cell 10 is selected in an image, then the same cell 10 is identified in the data plots and the data tables. FIG. 8B shows that when cells are selected 20 in a data plot, then the same cells are identified 20 in the image and the data tables.

The cell analysis program allows exporting of cells and the cell features for use with third party data analysis tools.

Calibration

The cell analysis program provides an automated calibration of the images acquired from different instruments to adjust for the variations in color. The color calibration profile defined for each instrument is applied to all pixels in an image prior to any analysis being performed.

Figure 9:
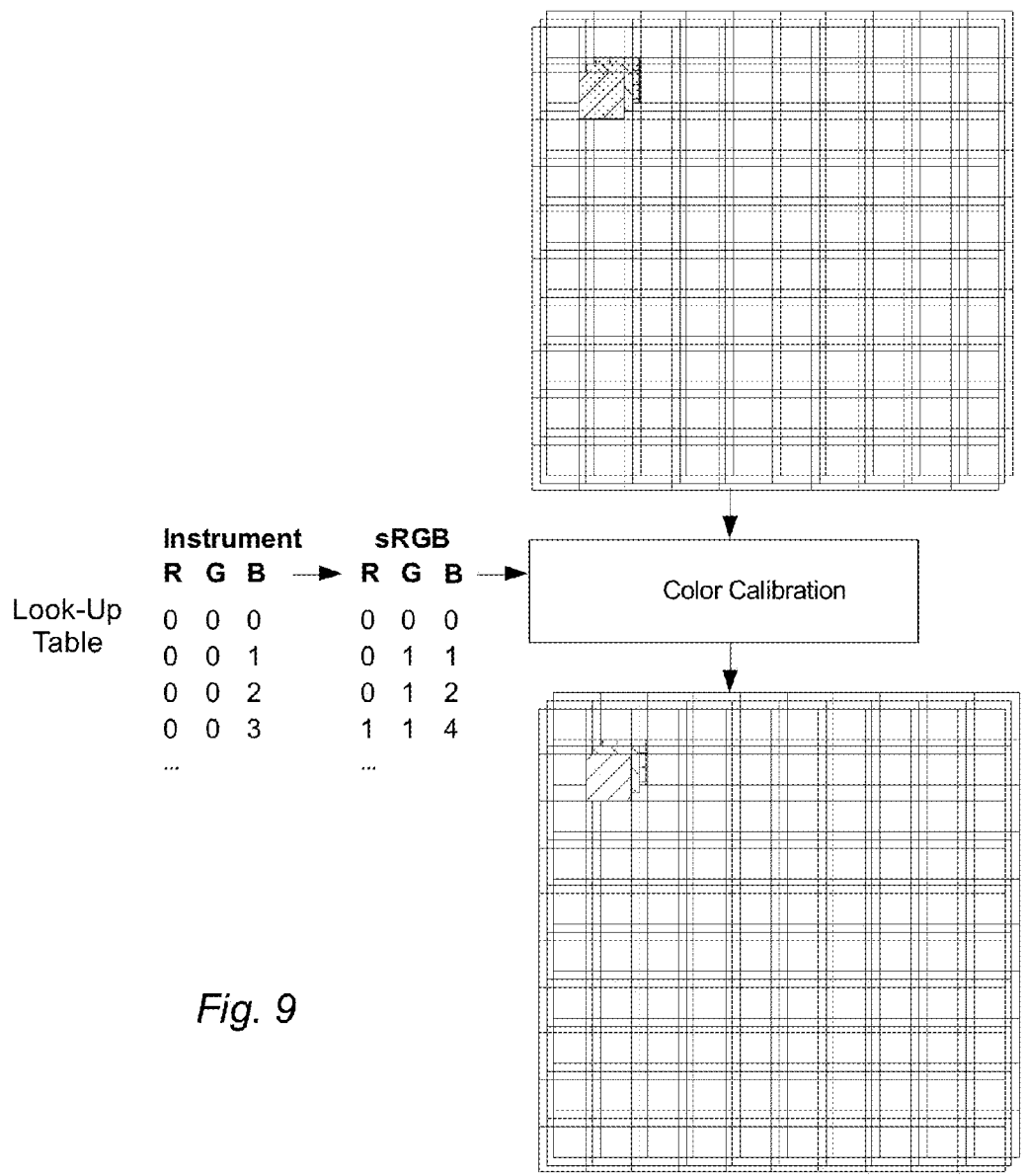
FIG. 9 illustrates the color calibration of images taken from different instruments using a color calibration profile.

FIG. 9 illustrates the color calibration of images taken from different instruments using a color calibration profile. A color calibration profile, in form of a look-up table, is used by a color calibration program to transform the RGB values of all pixels in the images from the instrument's RGB color space to a standard color space for the cell analysis, here the sRGB color space.

The cell analysis program provides an automatic calibration to adjust for the variations in the staining process by using standardized tissue-based or equivalent controls as part of the staining process. One way to use the controls for the calibration is to run the cell analysis program on the controls and then to adjust the data (e.g. cell feature measurements) or the parameters (e.g. cell feature detection thresholds, cell classification thresholds) based on the difference of the measured values and the established target values for the controls.

Figure 10:
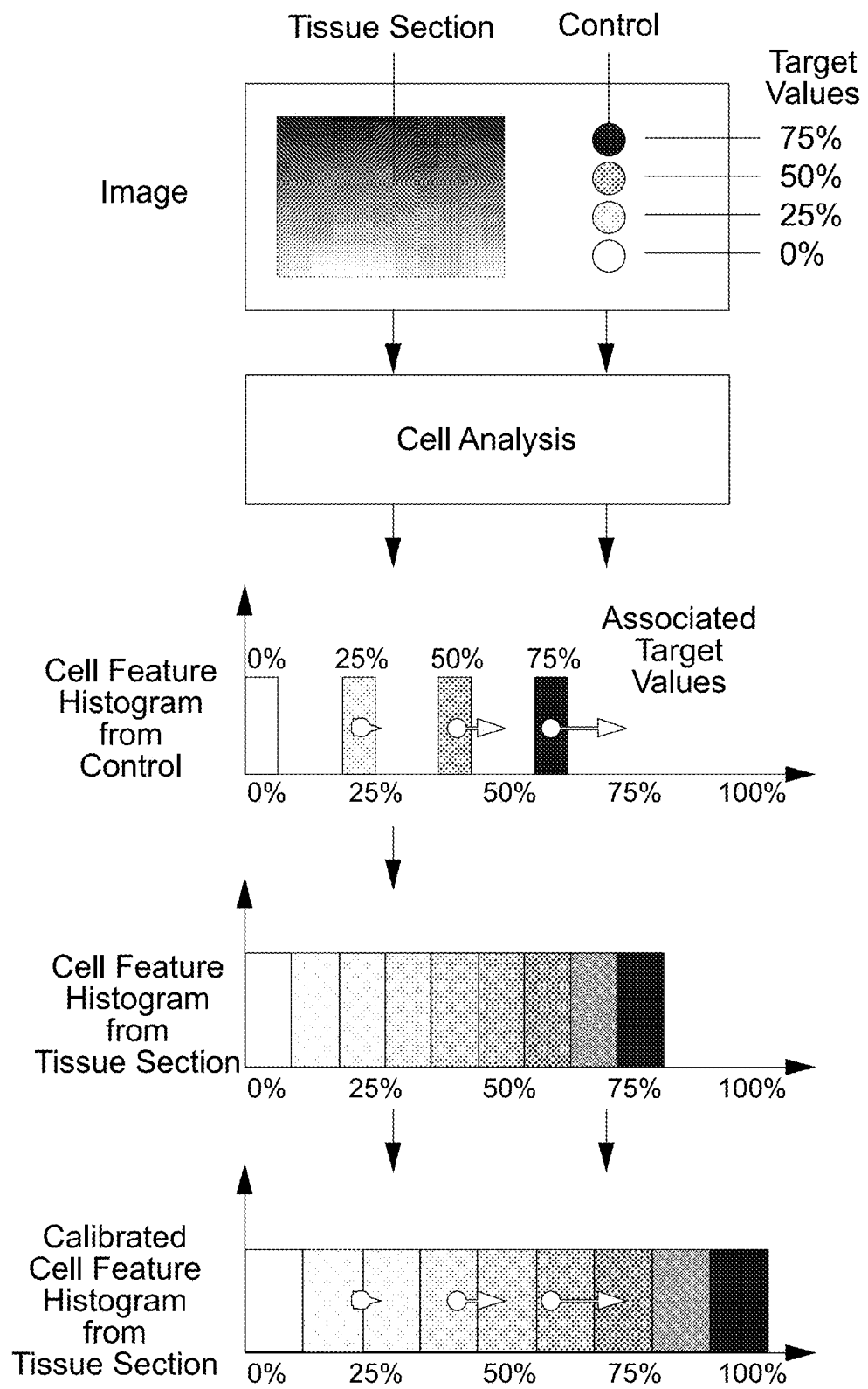
FIG. 10 illustrates the calibration of the cell analysis to the staining process using tissue-based or equivalent controls.

FIG. 10 illustrates the calibration of the cell analysis to the staining process using tissue-based or equivalent controls. The image of a slide contains the tissue section and the control. The different expression levels of a cell feature are shown as different intensities in the tissue section and the control. The tissue section can include the full range of a cell feature's expression levels. The control consists of four different samples with different established cell feature expression levels, here with the following target values of 0%, 25%, 50% and 75%. The cell analysis program is run on the control and the resulting histogram of the different control samples are shown with their associated target values. There are differences between the measured values and target values, which can be measured and used to define a calibration function. The cell analysis program is run on the tissue section and the resulting histogram of the cell feature is shown. Using the calibration function the cell feature measurements are adjusted and shown in the calibrated cell feature histogram of the tissue section.

Multiplexing

The standard for multiplexing cell features (e.g. IHC-HER2, IHC-ER and IHC-PR) has been at a histology slide level, combining the scores of the entire slides. The cell analysis program can provide multiplexing at the cell level.

Figure 11:
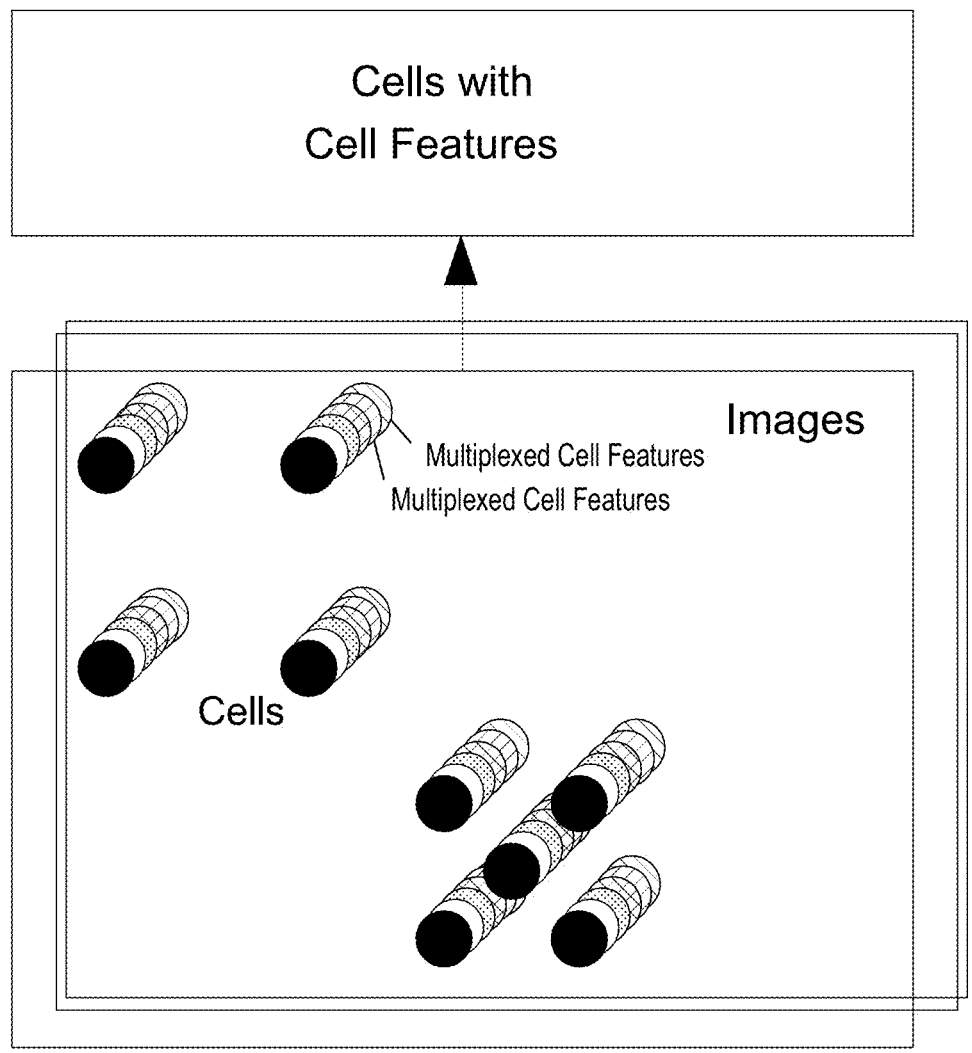
FIG. 11 shows the data hierarchy associated with a multiplexed cell analysis.
Figure 12A:
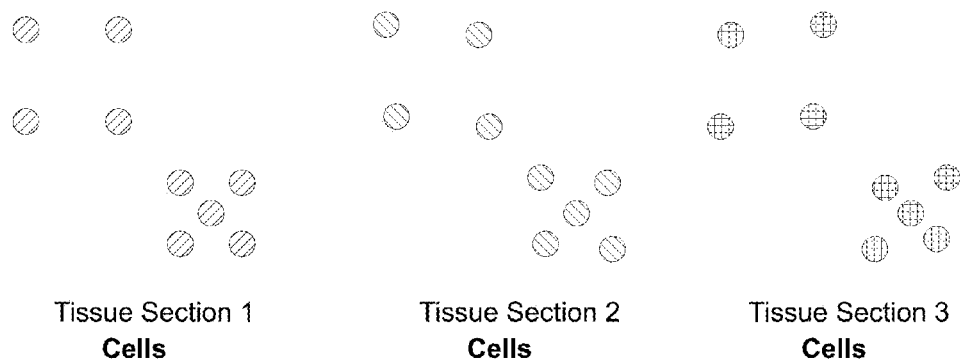
FIG. 12(A-D) illustrates the mapping of cell features across different tissue sections using a common grid.
Figure 12B:
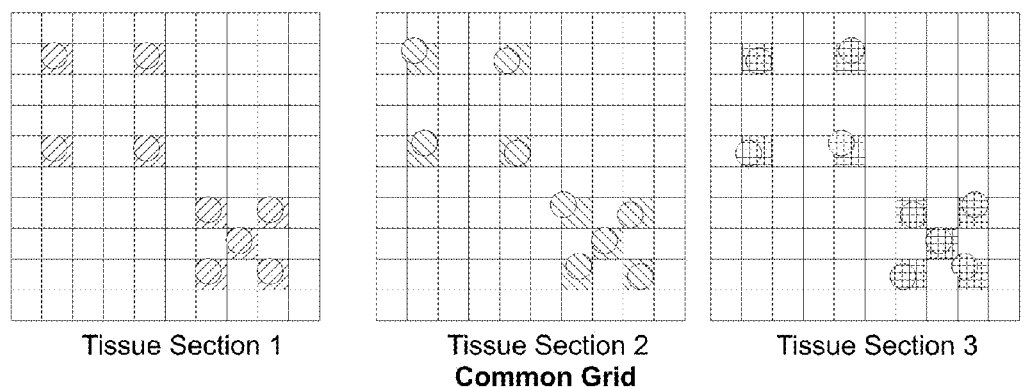
Figure 12C:
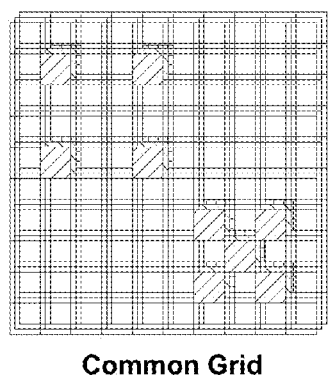
Figure 12D:
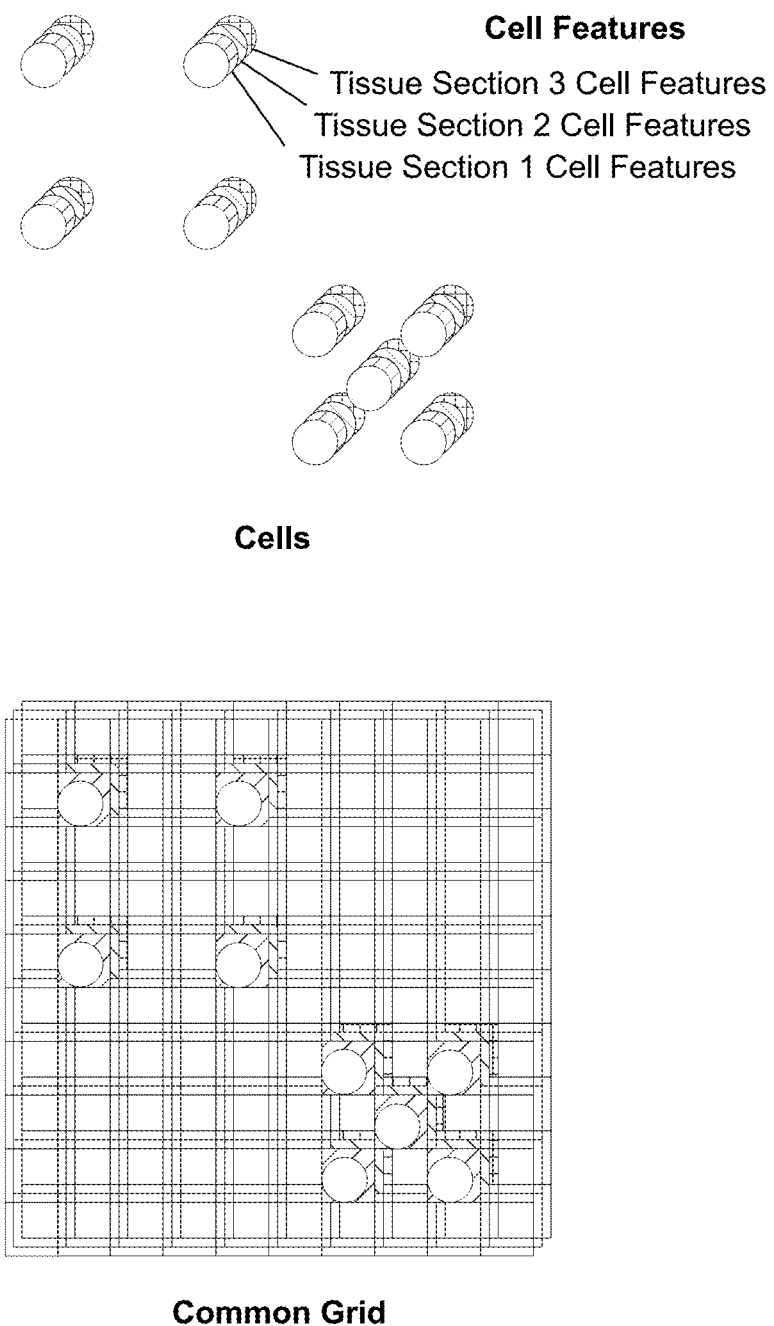

FIG. 11 shows the data hierarchy associated with a multiplexed cell analysis. The multiplexed cell features from the images of two different tissue sections are aligned and associated with the cells.

Cell features can be combined from images across different tissue sections using image registration techniques. The image registration provides a transform that calculates for any x, y coordinate in the image from one tissue section a new x, y coordinate in the image from another tissue section. Using the transforms, the image from one tissue section can be warped (i.e. spatially transformed) to align with the image from another tissue section, and the location and form of the cells detected in the image from one tissue section can be mapped to the image from another tissue section. In many cases, it makes sense to warp the images and map the cells with their cell features from all tissue sections (e.g. IHC-HER2. IHC-ER and IHC-PR) to a selected common tissue section (e.g. H&E).

Cell features can be combined from different images taken from the same tissue section using different imaging acquisition techniques (e.g. fluorescence and brightfield) without the use of sophisticated image registration techniques as those images are already perfectly aligned.

A visual linkage of the cell features from the images across the different tissue sections and/or different images from the same tissue sections can be provided by displaying the aligned warped images of the tissue sections together, by displaying a fused image from the aligned warped images of the tissue sections that can highlight certain cell features (e.g. brightfield H&E with fluorescence FISH-HER2), and by displaying the mapped cells with their cell features from the tissue sections overlaid on the image from a selected tissue section.

Multiplexing can be provided by combining the cell features across the different tissue sections. Different tissue sections do not necessarily include the same cells, so a 1:1 mapping of the cells and their cell features cannot be expected. But different tissue sections can be assumed to include the same tissue type regions with very similar cell features that will allow a reasonable alignment of the cell features. The tolerability for maximum distances from cell-to-cell across tissue sections which can be transformed into a single regional measurement carried across slides is dependent on the nature of the tissue architecture and the biological process represented by the analyte.

A common data structure is needed for the data alignment to map the cell features properly across different tissue sections. Appropriate area-based data structures include a common grid and cell-based data structures include virtual cells.

A common grid consists of surface areas (e.g squares, octagons) of a certain size that cover the entire tissue sections. The aligned cells from the different tissue sections are associated to individual surface areas based on their location.

Virtual cells are created based on the cells from the different tissue sections. The aligned cells from the different tissue sections are associated to individual virtual cells based on their proximity.

The common data structure inherits the cell features from the associated cells and vice versa. Multiple associations can be resolved by averaging the cell features. Smoothing is important for providing a means to reduce the variations in the cell features measurements. The cell features can be averaged using the cells in a certain cell neighborhood. Propagation is important for providing a means to compensate for the inaccuracies in the image registration and the variability of cell locations in different tissue sections. Using a common grid, the cell features of the individual cells can be propagated in the common grid in a certain distance around the cells. Using virtual cells, the propagation is implemented via proximity criteria.

The cell features from the cells detected in one tissue section can now be mapped to the cells detected in another tissue section using the common data structure. This way all the cell features from the different tissue sections can be mapped to the cells detected in a selected tissue section.

FIG. 12 illustrates the mapping of cell features across different tissue sections using a common grid. FIG. 12A illustrates the cells detected in the images from three different tissue sections. The cells are shown as circles with different patterns each representing colors (red, green, blue) illustrating the cell features from different tissue sections. FIG. 12B illustrates the mapping of the different cells and cell features from the different tissue sections to the squares in the common grid. FIG. 12C shows the common grid with all the different cell features. FIG. 12D illustrates how cells from one of the tissue sections or virtual cells 30 can be mapped to the common grid and the cell features from the common grid get associated with the cells.

FIG. 13 illustrates the mapping of cell features across different tissue sections using virtual cells. FIG. 13A illustrates the cells detected in the images from three different tissue sections. FIG. 13B illustrates how virtual cells 30 are created from the cells detected in the different tissue sections and how they inherit their cell features.

The common data structure with the cell features from the different tissue sections can be visualized in many different ways, including intensity/color-coded common structure representations and heatmaps overlaid on the image from a selected tissue section, 1D, 2D and 3D data plots and sortable and searchable data tables. The cell analysis program can allow exporting the common data structure with all the cell features for use with third party data analysis tools.

Cell Population Analysis

The cell population analysis program provides the examination of tissue samples based on the identification, characterization and interpretation of cell populations. The cell populations are used in order to facilitate the interpretation of a biological process. A cell population is defined as all cells that share a particular function of certain cell features. Tissue samples include one or multiple cell populations. Specific cell population features are calculated from the cells included in a cell population. The meta-data (e.g. species, tissue type, age, sex, conditions, drug dosage, clinical outcome) associated with a tissue sample varies depending on the purpose for the analysis.

Figure 14:
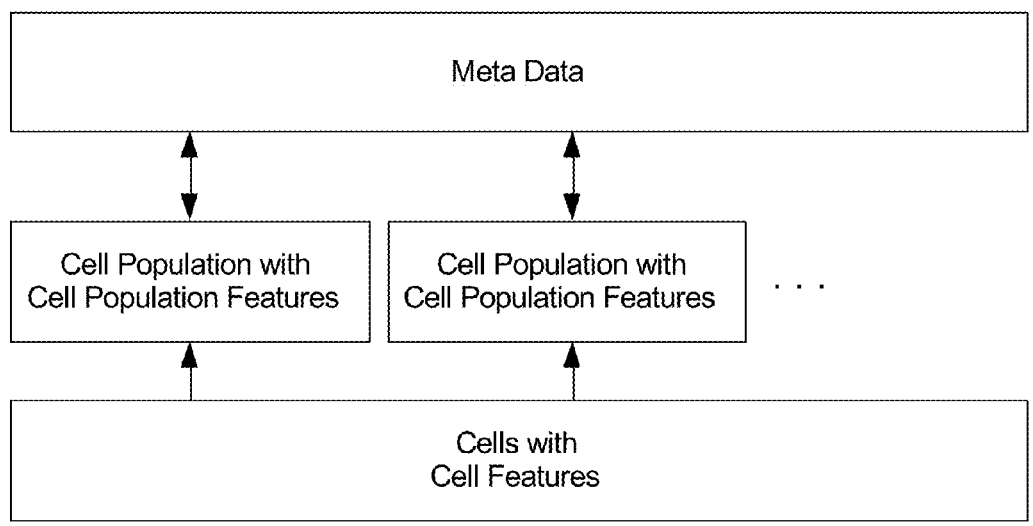
FIG. 14 shows the data hierarchy associated with the cell population analysis.

FIG. 14 shows the data hierarchy associated with the cell population analysis. Based on all the detected cells and the cell features in a tissue sample, one or multiple cell populations can be identified and specific cell population features can be calculated. The meta-data of a tissue sample is associated to all its cell populations.

The cell populations can be defined in many ways, which ultimately are specific to the intended outcome of the analysis. The definition of the cell population, which meets the target cell criteria, may be specific, statistical, representational, combinations thereof, or overall collections of defined subpopulations.

A specific definition results in a definition of a cell based on the specific characteristics of certain cell features. An example of a specific definition would be cells that are classified ER−, PR−, and HER2+, by defining thresholds for positivity for the biomarkers and including the cells that meet all three criteria.

A statistical definition is one that identifies a cell as being significant by its association with a specific tissue attribute or group of cells in the tissue. An example of a statistical definition may be the inclusion of a cell into the target population if it is defined as being in the stromal compartment, or in an area involved with heavy inflammation. This definition is mainly based on the characteristics of the cell neighborhood features that provide the structural and contextual tissue morphology of the cells in a defined area. The cells that meet the criteria, could be defined individually on each tissue section, and then combined across the tissue sections. The likelihood of each individual cell meeting the criteria could be defined by a statistical confidence.

A representational population may be one that is characterized by one or more histogram profiles of a measured cell feature. The histogram profile represents a unique population profile with information about the mean, standard deviation, and the presence or absence of subpopulations of cells. An example of a histogram profile is defining cells which are positive for a specific cell feature outside of one standard deviation from the mean, and thus represent a subpopulation of cells different from the expected profile of average cells across a tissue, regardless of the magnitude of measurement.

An example of a cell population definition, which relies on a combination of these approaches, could be described as "inflammatory cells present in the highest HER2 expressing tumor nests". Here, a cell would be described specifically as inflammatory by a nuclear size threshold defining a small nuclei characteristic of an inflammatory cell; and described representationally as being a cell with a high HER2 expression, and described statistically as being in a tumor nest if the cells within a certain area were statistically comprised of tumor cells.

One possible cell population classification scheme that would facilitate a standardization of the data sets in a database is based on biology motivated cell types (e.g. invasive tumor cells, carcinoma in-situ cells, stroma cells, normal cells) in combination with the species (e.g. human) and tissue type (e.g. breast tissue) information from the meta-data of the tissue samples. Special cell populations required for the specific analyses could then be implemented as subpopulations of those cell populations or as part of the cell population features.

Identification

The key to identifying cell populations is to identify the important cell features and define the appropriate function of those cell features that define the cell population.

Uni-, Bi- and Multivariate Analysis

It is important to understand the relationship between the different cell features (e.g. membrane staining intensity vs. membrane completeness) and their relevance for the identification and/or quantification of certain cell characteristics that are meaningful for the interpretation of tissue samples (e.g. different cell types or cells with a certain protein expression profiles). The different cell features can be thought of as statistical variables.

The cell population analysis program can provide uni-, bi- and multivariate analysis (incl. probability distribution statistics) and visualization applied to statistical variables. Linear and non-linear component analysis and dimensionality reduction techniques (e.g. Pearson's product-moment coefficient, linear regression) can be used to understand the relationships between variables and their relevance to the actual problem under investigation. Unsupervised and supervised machine learning techniques can be used to identify relationships between the variables.

Figure 15:
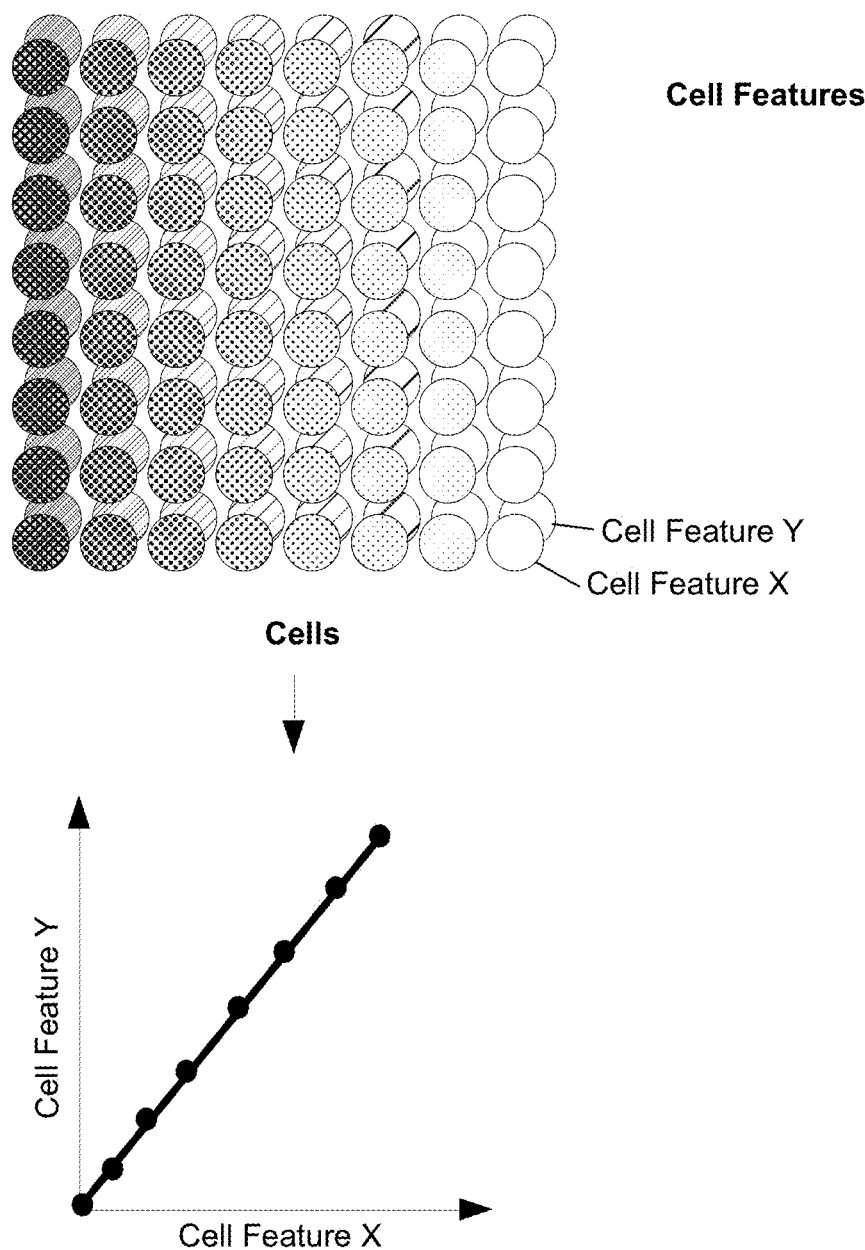
FIG. 15 illustrates a linear regression analysis of two cell features.

FIG. 15 illustrates a linear regression analysis of two cell features. The detected cells in the image from a tissue section are illustrated as a grid of circles. The cells are shown with two cell features "X" and "Y". The circles are intensity-code based on the value of the cell feature. A 2D scatter plot and linear regression of the cell feature "X" and "Y" are shown.

Alternatively to a cell-based analysis, the common grid (even when using only a single tissue section) can be used to create an area-based analysis and map the data back and forth between an area-based and a cell-based representation.

The analysis can include data from multiple tissue samples (or different blocks from the same tissue sample), in which case the tissue samples' meta-data can be thought of as additional statistical variables. The cells from different tissue samples can be visualized distinctively (e.g. color-coded) in the analysis. The cells and cell features from multiple tissue samples as well as the images of the tissue sections can be conveniently stored and accessed from a database.

Figure 16:
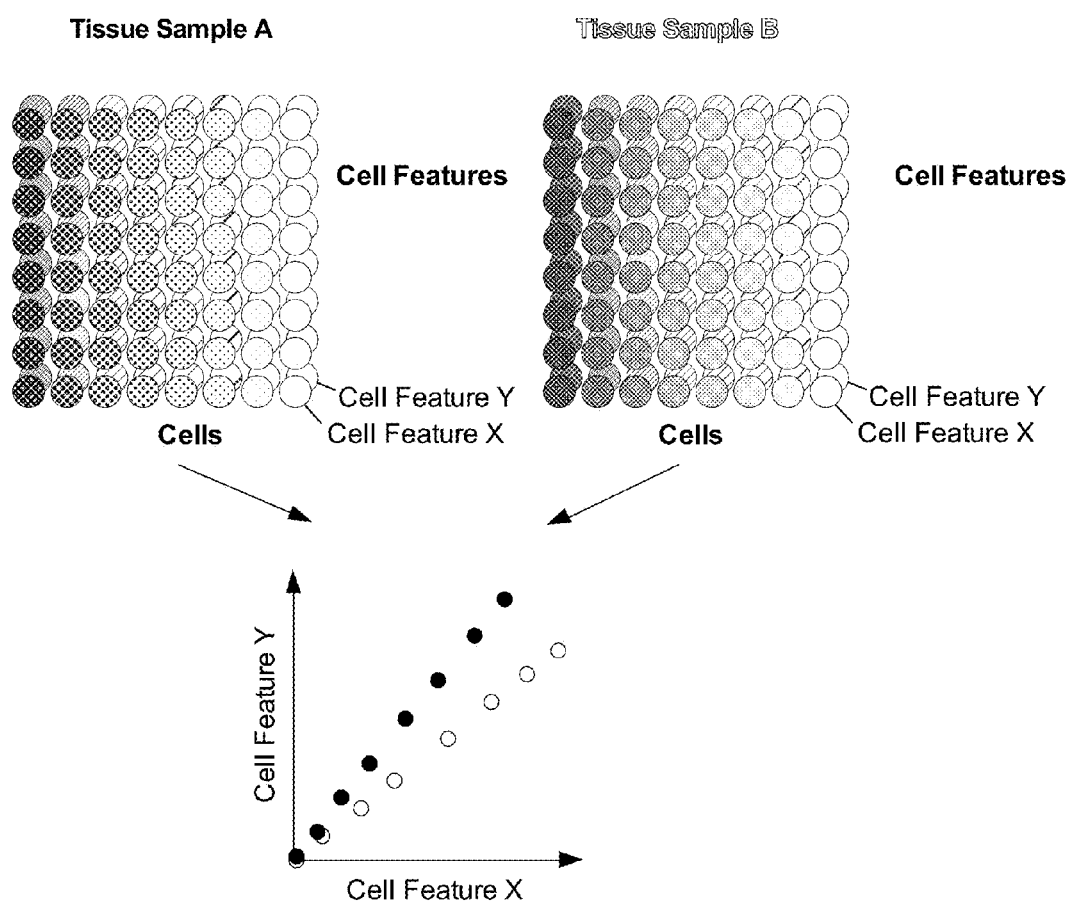
FIG. 16 illustrates an analysis based on cells from different tissue samples.

FIG. 16 illustrates an analysis based on cells from different tissue samples. The cells from two tissue samples "A" and "B" are shown with the same cell features "X" and "Y". A 2D scatter plot of the cell features "X" and "Y" shows the cells from the two tissue sections in different colors (black—tissue sample A, and white—tissue sample B).

The intuitive or empirical knowledge about the target cells can be provided through cell annotations that can be thought of as additional statistical variables. Cell annotations are created by identifying examples of cells and associating them with certain labels or values.

Figure 17:
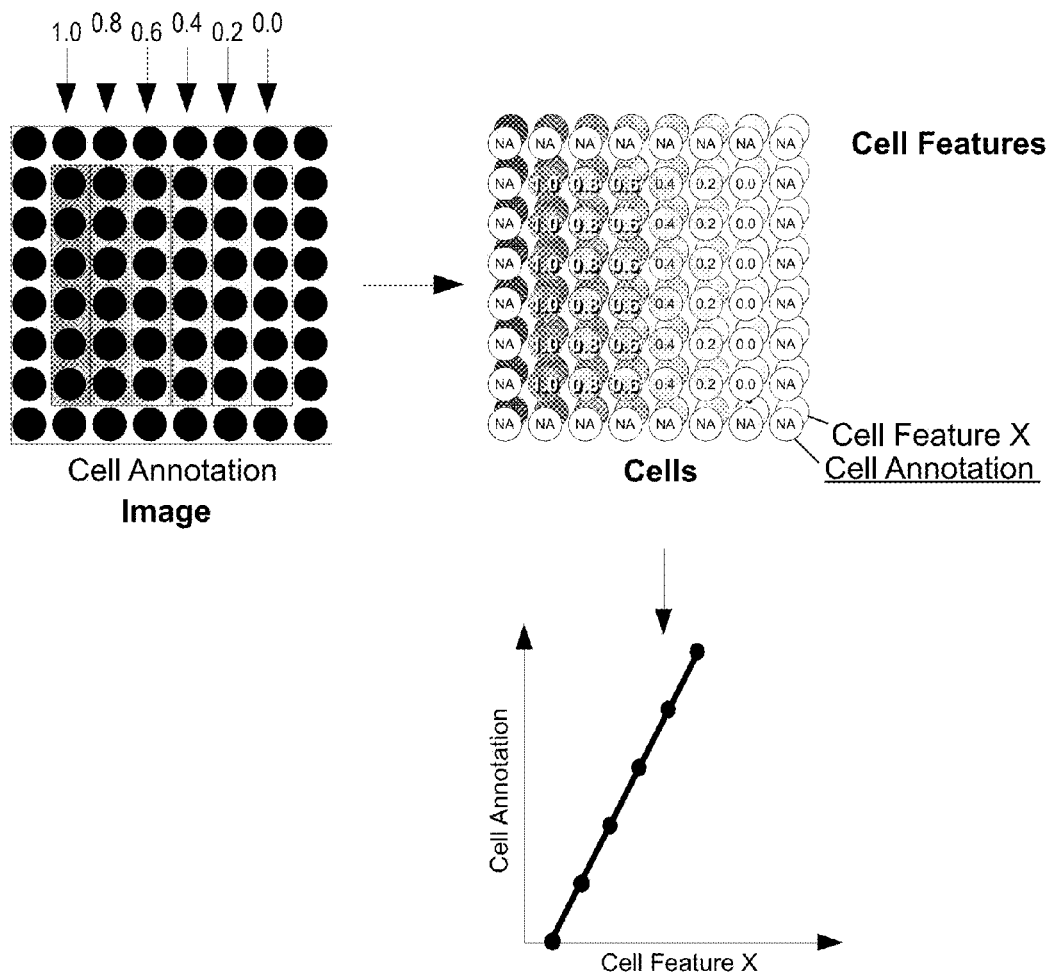
FIG. 17 illustrates the creation of a cell annotation.

FIG. 17 illustrates the creation of a cell annotation. Multiple regions-of-examples can be defined for a cell annotation in an image from a tissue section and provides for each region an associated value. The regions-of-examples are intensity-coded based on the associated value. A new cell feature is created for the cell annotation. Now the cell annotation can be used in the same way as the measured cell features, as shown with the 2D scatter plot and linear regression of the cell feature "X" and the cell annotation.

The cell population analysis program can provide the capability to define new cell features that are calculated from existing cell features. Those new cell features can be used to identify and quantify certain cell characteristics that are meaningful for the interpretation of tissue samples (e.g. certain cell protein expression profiles). New cell classification, scoring and interpretation schemes can be created based on or including those new cell features.

How a new cell feature is calculated is defined using different calculation models, including linear and non-linear functions, template similarities (e.g. normalized sum of absolute differences) and any algorithm (e.g. program code implementation) that calculates a new value from a set of values.

Supervised machine learning techniques can assist in the calculation of a new cell feature, which is determined automatically based on user-provided cell annotations.

Figure 18:
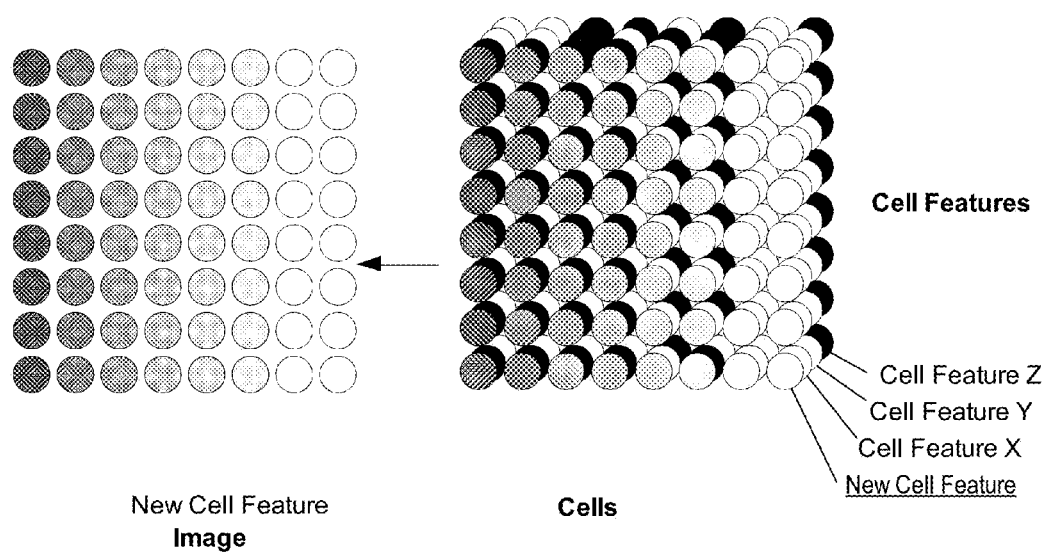
FIG. 18 illustrates the creation of a new cell feature.

FIG. 18 illustrates the creation of a new cell feature. A calculation model is provided that calculates a new cell feature based on the cell features "X", "Y" and "Z". A new cell feature is created. Now the new calculated cell feature can be used in the same way as the measured cell features, as shown with the visualization of the new cell feature in an image from a tissue section.

A possible application would be to implement the 5-year survival statistics based on the HER2, ER and PR expression levels published in [1] as a new cell feature. The cell feature can be calculated based on the data points from the publication (ER+/PR+/HER2− 96.4%, ER+/PR−/HER2− 91.9%, ER+/PR+/HER2+ 91.3%, ER+/PR−/HER2+ 88.0%, ER−/PR+/HER2− 82.7%, ER−/PR+/HER2+ 78.8%, ER−/PR−/HER2− 76.2%, ER−/PR−/HER2+ 75.9%) and a linear approximation between the data points. Now using the cell data of the 5-year survival statistics over all invasive tumor cells can be investigated for the basis of a new scoring scheme.

Manual Gating

The cell population analysis program can provide manual gating, whereby cell populations are identified by defining sequential gating functions of selected cell features. Manual gating typically supports a specific definition of cell populations.

Regions-of-examples for the different cell populations in the images can be defined from the tissue sections to identify representative cells with their cell features. Those identified cells and their association to certain cell populations can be visualized (e.g. separate plots, color-coded) in the gate definition process. All cells or only those cells from the regions-of-examples can be selected for use in the gate definition process.

One-, two- or three-dimensional graphical representations of selected cell features are used to identify the regions (e.g. min./max., multiple polygons) of the cells of interest. A sequence (or hierarchy) of intersections and unions of those regions definitions of one to three cell features can be created to define a cell population. The sequential gating function can be incrementally created, at each step only looking at the resulting cells from the previous step.

A very simple and effective way to create a gating function is to use a marker stain for a certain cell type and to gate on the cell feature that measures the marker stain. Using multiplexing, a marker stain can be used for a certain cell type on one tissue section and thereby identify that cell type on all other tissue sections.

The cells corresponding to the cell populations can be identified at the same time in the images from the tissue sections.

Figure 19A:
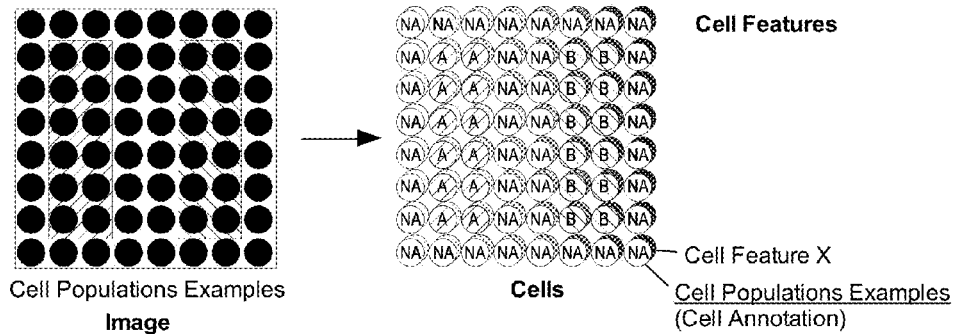
FIG. 19(A-C) illustrates the gate definition process using representative cells for the different cell populations.
Figure 19B:
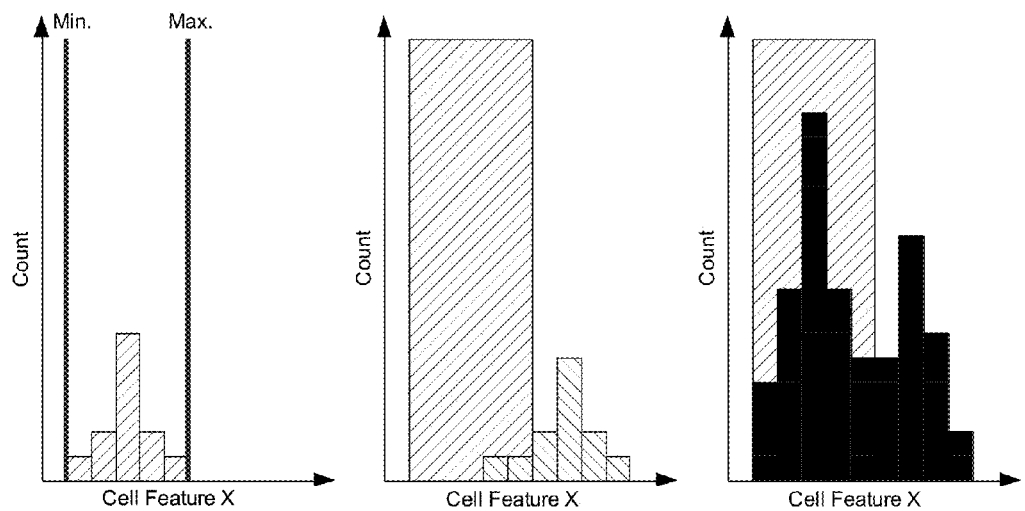
Figure 19C:
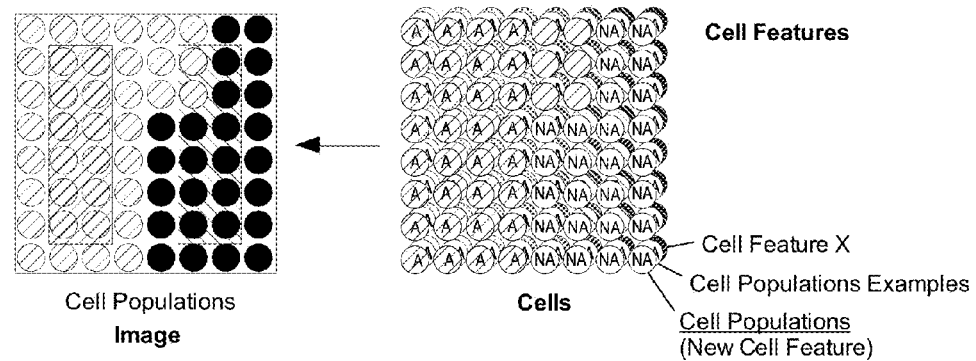

FIG. 19 illustrates the gate definition process using representative cells for the different cell populations. The detected cells in the image from a tissue section are illustrated as a grid of black or patterned circles. The graphical representation of a single cell feature is shown as a 1D histogram. FIG. 19A illustrates the defining of two regions-of-examples 40; 50 for two cell populations of interest and the creation of a new cell annotation for the cell population examples. FIG. 19B illustrates a gate definition step, which defines a minimum and a maximum threshold for the cell feature "X". In addition to a plot that includes all cells, separate plots for each cell population containing only the cells from the corresponding regions-of-examples 40; 50, respectively, are shown. The region definition 41 (min. and max.) from the "to be defined" cell population 40 is shown in the other plots as well. FIG. 19C illustrates the creation of a new cell feature for the cell populations and shows the pattern-coded cells 40 from the "to be defined" cell population in the image.

The gate definition process can include multiple tissue samples. This allows taking the variations between tissue samples into account. The cells from different tissue samples can be visualized (e.g. separate plots, color-coded) in the gate definition process. The tissue samples' cells and cell features as well as the images of the tissue sections can be conveniently stored and accessed from a database.

The cell population analysis program allows using a defined gating function for the automated gating of cells in different tissue samples.

Pattern Recognition

The cell population analysis program can provide cell-based pattern recognition, based on supervised machine learning techniques, for the automatic classification of the cell into the different cell populations. Pattern recognition is typically used for a specific and statistical definition of cell populations. The machine learning technique used determines how important cell features are identified and what kind of calculation model will be used for the cell classification. The cell classification can be expressed using class labels (i.e. a cell can only be part of one cell population) or class probabilities (i.e. a cell can be part of multiple cell populations).

Regions-of-examples for the different cell populations in the images from the tissue sections can be defined to identify representative cells with their cell features.

The pattern recognition tool identifies the important cell features and determines the cell classifier based on the provided regions-of-examples.

Alternatively or in combination to cell-based pattern recognition, the common grid (even when using only a single tissue section) can be used to perform area-based pattern recognition and map the data back and forth between an area-based and a cell-based representation.

The cells corresponding to the different cell populations can be identified in the images of the tissue section.

Figure 20A:
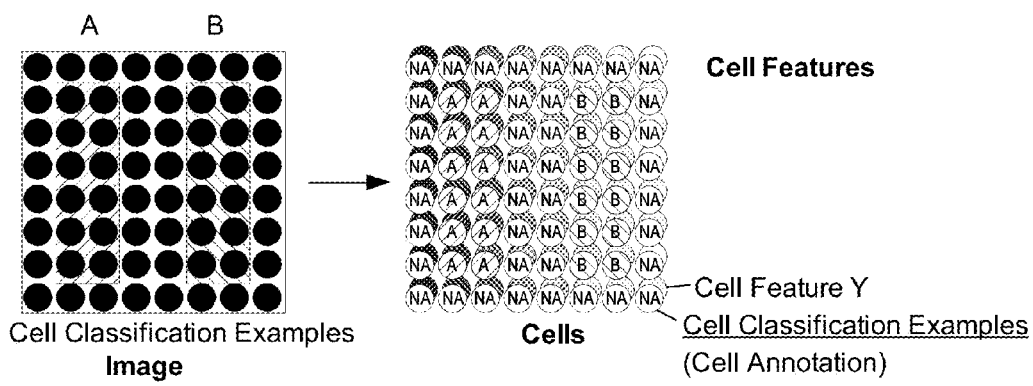
FIG. 20(A-B) illustrates the pattern recognition process using representative cells for the different cell populations.
Figure 20B:
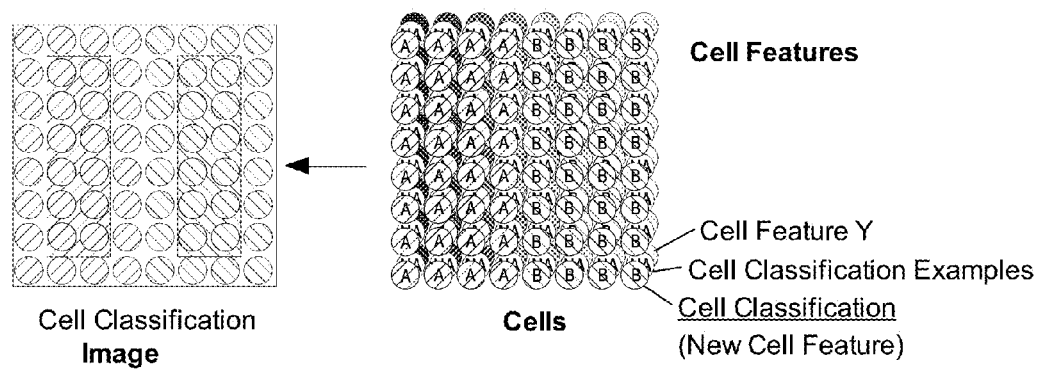

FIG. 20 illustrates the pattern recognition process using representative cells for the different cell populations. FIG. 20A illustrates the defining of two regions-of-examples 60; 70, respectively, for two cell classifications of interest and the creation of a new cell annotation A, B, NA, respectively for the cell classification examples. FIG. 20B illustrates the creation of a new cell feature for the cell classification and shows the pattern-coded cells A; B from the two cell classes in the image.

The pattern recognition can include multiple tissue samples. This allows taking the variations between tissue samples into account. The tissue samples' cells and cell features as well as the images from the tissue section can be conveniently stored and accessed from a database.

The cell population analysis program allows using a defined cell classifier for the automated classification of cells in different tissue samples.

Population Mixture Model Analysis

The cell population analysis program provides population mixture model analysis, including unsupervised machine learning techniques (e.g. Gaussian mixture model), for the automatic classification of the cell into the different cell populations. Population mixture model analysis is typically used for a representational definition of cell populations. A mixture model is a probabilistic model for representing the presence of cell subpopulations within an overall cell population. Mixture models are used to make statistical inferences about the properties of cell subpopulations given only observations from the overall cell population. Different kinds of distribution models can be used including, a Gaussian model.

Population Comparison

The cell population analysis program provides population comparisons, based on the comparison of cell population cell features' distribution functions and cumulative distribution functions (CDF). Different cell populations within the same tissue section or across different tissue sections can be compared to define a representational cell population.

Cell Population Features

Tissue samples are characterized by different cell populations and their cell population features. Once the cell populations are identified, cell population features (e.g. percentage of cells with respect to the total number of cells, statistics of cell features and cell feature histograms) are calculated from the cells and the cell features for each cell population.

Interpretation

The interpretation of cell populations deals with the comparison of tissue samples and the predication for tissue samples.

Databases

Looking at the data from tissue samples across a study or an institution or in the context of large populations provides new insights and a new perspective on the data.

The data set of a tissue sample can include the meta-data (e.g. species, tissue type, sex, age, conditions, drug dosage and clinical outcome), the cell populations with their cell population features (e.g. percentage of cells with respect to the total number of cells, statistics of cell features and cell feature histograms), but can also include the cells with their cell features and the images of the tissue sections.

The key is to provide an infrastructure that allows creating, managing and accessing multiple tissue sample databases. An institution could have its own central database and access other public databases. Databases can be on a local computer, on a central server on a network (incl. virtual private networks) and/or be implemented as a cloud application.

A standardization of the data sets for the tissue samples is important for the utility of the databases.

Data Mining and Visualization

Data mining techniques, including unsupervised and supervised machine leaning techniques, and visualization techniques, including heatmaps, 1D, 2D and 3D data plots and sortable and searchable data tables, can be used with the databases to automatically or semi-automatically analyze large quantity of data. The goal of data mining and visualization is to extract previously unknown interesting patterns such as groups of data sets (cluster analysis), unusual data sets (anomaly detection) and dependencies (association rule mining), and to be able to provide predications for data sets in form of classification or regression analysis.

FIG. 21 illustrates a heatmap for tissue samples from a database. The rows in the heatmap represent the different characteristics and the columns the different records. Specific meta-data, cell populations and cell population features are selected in the "Select Items" category. The "Options" category allows limiting the range of the characteristics and to define the way the data should be displayed in the heatmap (e.g. values, color- or intensity-coded). The heatmap is limited to a certain species and tissue type. The "Sort" category allows sorting the data by characteristics. The black boxes illustrate the capability to access the complete information for a tissue sample. In addition to the meta-data and the cell population data in the heatmap, access to the corresponding cell data and the images is provided.

Additional knowledge or assumptions about the tissue samples can be included in the analysis by simply adding the information to the meta-data.

Decision Support System

The cell population analysis program can include a decision support system based on the tissue analysis data and related meta-data of a tissue sample under investigation. The decision support system can provide a similarity analysis that allows quantifying and visualizing (e.g. heatmaps) the differences in the tissue analysis data (e.g. human—breast tissue—invasive tumor cell population—HER2, ER and PR expressions) and meta-data from a tissue sample under investigation and data sets from a database with known conditions or outcome (e.g. survival after different treatment options). The decision support system can provide access to the slide images, the cells with their cell features, the cell populations with their cell population features and related meta-data, as well as additional case information, including data from other modalities (e.g. radiology data), for the data sets in the database. This allows answering questions such as, how close is the data to that of known conditions or outcome.

A simple way to implement a decision support system based on a similarity analysis is to expand the heatmap as shown in FIG. 21 with a similarity criterion (e.g. weighted sum of absolute differences) for selected meta and cell population data. The heatmap can now show a tissue sample under investigation in the context of similar tissue samples in the database.

Rather than providing a decision support system based on the actual data sets in a database, a special data set can be created for a decision support system that is based on a synthesis of clinical findings and example cases. The tissue sample under investigation can now be shown in the context of all the different significant characterizations of a case with possible decisions and to be expected outcome.

A possible application would be to use the 5-year survival statistics based on the HER2, ER and PR expression levels published in [1] for the synthesis of clinical findings and to select representative and interesting cases as examples. Eight cases could be created based on the data points from the publication (ER+/PR+/HER2− 96.4%, ER+/PR−/HER2− 91.9%, ER+/PR+/HER2+ 91.3%, ER+/PR−/HER2+ 88.0%, ER−/PR+/HER2− 82.7%, ER−/PR+/HER2+ 78.8%, ER−/PR−/HER2− 76.2%, ER−/PR−/HER2+ 75.9%).

Automatic Meta-Data Prediction

The cell population analysis program can provide the capability to predict meta-data based on a tissue sample's cell populations and the cell population features. Supervised machine learning techniques can be used to learn the classifier from tissue sample examples with the existing meta-data.

A possible application is the prediction of the species and tissue type as the cell and cell population analysis is species and tissue specific. The information about the species (e.g. human) and tissue type (e.g. breast tissue) is typically provided with the tissue sample. The cell population analysis program can also predict this information automatically by comparing the cell populations of the tissue sample with known species-tissue type cell populations.

In Vitro Diagnostic Multivariate Index Assays (IVDMIA)

IVDMIAs can be defined and implemented based on the tissue samples' cell population features (e.g. HER2 expression, ER expression, PR expression) from one (e.g. invasive tumor cells) or multiple cell populations (e.g. stroma cells) and related meta-data (e.g. age, sex, conditions).

Uni-, bi- and multivariate analysis and data mining and visualization can be used to identify common patterns and to determine the important features and their relationship to clinical outcome.

New scoring and interpretation schemes can be defined using different calculation models, including linear and non-linear functions, template similarities (e.g. normalized sum of absolute differences) and any algorithm (e.g. program code implementation) that calculates a new value from a set of values.

An approach for defining an IVDMIA involves the use of profile histograms to define the characteristics of cell population features used to determine the IVDMIA. An example of a profile histogram is a dataset that displays the mean value of Y and its root mean square (RMS) for each bin in X. Each Y parameter would be chosen from the cell population features. Each X parameter is arbitrary, and may be a related, a non-obviously related or unrelated dataset of criteria related to the cell-based tissue analysis approach. In this case, the included X and Y values are plotted in the profile histogram to create a unique pattern which represents a specific IVDMA output. This pattern captured in the IVDMIA output is correlated to the meta-data in a fashion that specific IVDMIA output patterns (profile histogram) are predictive of a clinical output related to the meta-data. For example, this profile histogram, or a range of similar profiles, could be used to define a binary (yes/no, positive/negative, etc) output of the IVDMIA which has prognostic or diagnostic value. Thus, the IVDMIA captures the multi-dimensional outputs of the cell-based tissue analysis, and captures it in a summary format that is amenable to algorithmic determination of an output with direct application for the IVDMIA.

A possible application would be to implement the calculation of the 5-year survival statistics based on the HER2, ER and PR expression levels as published in [1]. A simple calculation model could be to use the data points from the publication (ER+/PR+/HER2− 96.4%, ER+/PR−/HER2− 91.9%, ER+/PR+/HER2+ 91.3%, ER+/PR−/HER2+ 88.0%, ER−/PR+/HER2− 82.7%, ER−/PR+/HER2+ 78.8%, ER−/PR−/HER2− 76.2%, ER−/PR−/HER2+ 75.9%) and to provide a linear approximation between the data points.

New scoring and interpretation schemes can be determined automatically, assisted by supervised machine learning techniques and based on selected tissue samples with corresponding meta-data (e.g. clinical outcome).

Calibration

The cell population analysis program can provide an automatic calibration of the cell population features (e.g. HER2, ER, PR expressions) to adjust for the variations in the tissue and slide preparation process by comparing the detected cell populations and their cell population features to a norm. A norm can be established from tissue sections that have been prepared using controlled procedures varying the different tissue and slide preparation parameters (e.g. varying fixation time) and/or analyzing the data sets from large populations. This kind of calibration can be thought of as using internal tissue controls all the way from a biopsy to the final analysis.

An approach for defining a calibration output involves the use of profile histograms to define the characteristics of cell population features to determine the calibration output values. Each Y parameter would be chosen from the cell population features. Each X parameter is a criteria related to the cell-based tissue analysis approach. In this case, the included X and Y values are plotted in the profile histogram to create a unique pattern which represents a specific calibration output. If the profile histogram falls within a defined range of the predetermined normal standard, then the assay used to create the sample is considered properly calibrated. This approach can be used to assess all points in the tissue and slide preparation process.

Quality Assessment

Artifacts from the tissue and slide preparation, digitization, or other factors may confound the tissue analysis and lead to errors. Therefore, quality assessment is a crucial step of the tissue analysis. The quality assessment includes the measurements of inter tissue sample variability and the detection of variations that are not likely biologically motivated. Biologically motivated variations can be defined by analyzing the data sets from the target population.

An approach for defining a quality output involves the use of profile histograms to define the characteristics of cell population features used to determine the quality output values. Each Y parameter would be chosen from the cell population features. Each X parameter is a criteria related to the cell-based tissue analysis approach. In this case, the included X and Y values are plotted in the profile histogram to create a unique pattern which represents a specific output. If the histogram profile falls within an empirical or intuitively defined range of normalcy, then the sample meets the quality standards. An example of an intuitive definition of the defined range normalcy may be subjective to a pathologist interpretation. An example of an empirical definition of the defined range of normalcy may be inclusion of the sample within one standard deviation of the mean of population of all samples analysed using the same methodology.

Figure 22:
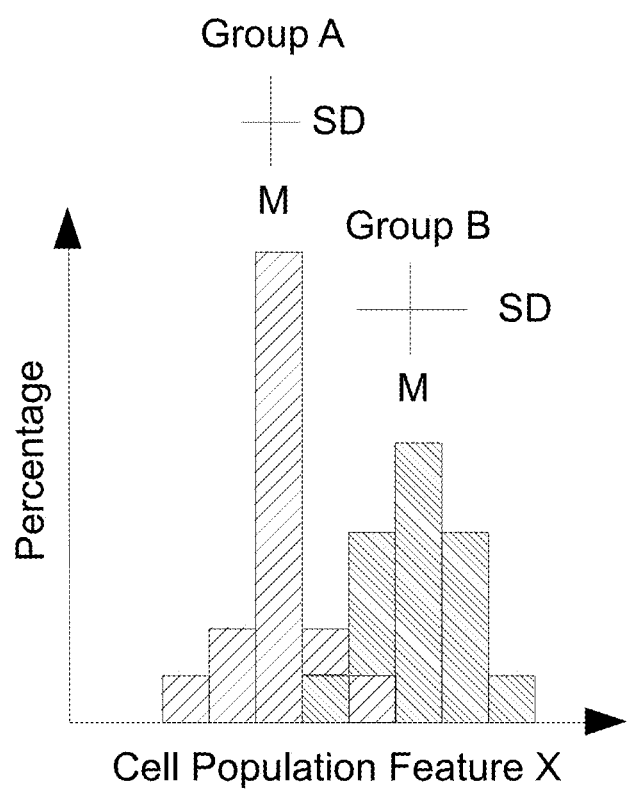
FIG. 22 illustrates quality assessment based on the comparison of cell population feature distributions from different groups.

FIG. 22 illustrates quality assessment based on the comparison of cell population feature distributions from different groups. The cell population feature distributions for the same cell population feature "X" are shown for two different groups "A" 80 and "B" 90 in the same 1D data plot. It can easily be seen that the distributions are different in terms of their mean (M) and standard deviation (SD). Additional statistical tests can provide clear acceptance criteria.

A possible application would be to compare the distribution of protein expressions (e.g. HER2, ER and PR) of a study or institution to the distribution of the same protein expressions in the target population. There could be international, national and regional databases that accumulate and provide the data sets from the target populations.

We claim:

1. A method for cell-based tissue analysis, comprising:
obtaining consecutive tissue sections from a tissue sample, the consecutive tissue sections having consecutive relation associated therewith, mounting each of the tissue sections on one of a plurality of histology slides, and independently staining each of the tissue sections with a histology stain;
acquiring a digital image for each of the plurality of histology slides containing the independently stained consecutive tissue sections, wherein a plurality of digital images are obtained for the plurality of corresponding histology slides or portions thereof;
associating each of the digital images with its corresponding independently stained consecutive tissue sections in relation to the tissue sample;
detecting cells within one or more of the digital images, with the detected cells:
  measuring one or more cell features of the detected cells with respect to each image and each histology stain associated therewith, said cell features comprising: cell morphology, cell expressions, staining characteristics, cell neighborhood characteristics, cell region characteristics, or a combination thereof,
  multiplexing the measured cell features across the digital images of adjacent tissue sections to assemble three-dimensional cell-based data, and
  representing the cell-based data on a computerized display using interactive computer-generated visualizations;
identifying cell populations within the three-dimensional cell-based data, said cell populations comprising one or more groups of cells categorized by having the one or more measured cell features representative of said cell populations, and with the identified cell populations:
measuring one or more cell population features,
categorizing cell subpopulations within the identified cell populations based on the one or more measured cell population features, and
representing the cell subpopulations on a computerized display using interactive computer-generated visualizations; and
storing information associated with the detected cells, cell features, cell populations, and cell population features in one or more databases for subsequent comparative analysis.

2. The method of claim 1, wherein said cell population features comprise: a percentage of cells with respect to the total number of cells in a selected region of the digital images, statistics of cell features within the digital images, and cell feature distribution, or a combination thereof.

3. The method of claim 1, wherein said multiplexing comprises mapping the cells and the cell features about the digital images of adjacent tissue sections.

4. The method of claim 1, wherein said identifying cell populations includes one of: uni-variate, bi-variate, and multi-variate analysis.

5. The method of claim 1, wherein said cell populations are identified using sequential gating, pattern recognition, population mixture model analysis, or population comparisons based on the comparison of cell populations' cell features' distribution and cumulative distribution functions.

6. The method of claim 1, wherein said interpreting cell populations provides: data mining and visualization; decision support systems that are based on a similarity analysis of tissue samples under investigation with data sets in the data bases; automatic predication of meta-data based on a tissue sample's cell populations and their cell population features using machine learning techniques; or a combination thereof.

7. The method of claim 1, wherein said interpreting cell populations allows for the definition of an in vitro diagnostic multivariate index assays (IVDMIA) for tissue samples from one or more cell populations, cell population features and related meta-data.

8. The method of claim 7, wherein said definition of the in vitro diagnostic multivariate index assays (IVDMIA) is defined using machine learning techniques.

9. The method of claim 1, wherein calibration of the cell features and cell population features is performed for variations in the tissue and slide preparation process by comparing the detected cell populations and the cell population features to a norm established using controlled procedures varying tissue and slide preparation parameters or analyzing data sets from large populations.

10. The method of claim 1, wherein said interpreting cell populations provides a quality assessment that measures inter tissue sample variability.

11. The method of claim 1, wherein said computer-generated visualizations comprise one or more of: interactive linkage between data and display, image overlays, heatmaps, data plots, 3D displays of aligned images, fused images from aligned images and mapped cell data and image overlays of mapped cell data onto an image from a different tissue section.

* * * * *